(12) United States Patent
Abellon et al.

(10) Patent No.: US 9,074,194 B2
(45) Date of Patent: Jul. 7, 2015

(54) SEQUENCE OF NUCLEOTIDES AND PEPTIDES GSE 24.2 OF DYSKERIN, WHICH CAN INDUCE TELOMERASE ACTIVITY, METHOD FOR OBTAINING SAME, THERAPEUTIC COMPOSITIONS AND APPLICATIONS THEREOF

(75) Inventors: Rosario Perona Abellon, Madrid (ES); Rosario Machado Pinilla, Madrid (ES); Leandro Sastre Garzon, Madrid (ES); Isabel Sanchez Perez, Madrid (ES); Jose Ramon Murguia Ibanez, Valencia (ES)

(73) Assignees: CONSEJO SUPERIOR DE INVESTIGACIONES CIENTIFICAS, Madrid (ES); UNIVERSIDAD AUTONOMA DE MADRID—FUNDACION GENERAL, Madrid (ES); UNIVERSIDAD POLITECNICA DE VALENCIA, Valencia (ES)

( * ) Notice: Subject to any disclaimer, the term of this patent is extended or adjusted under 35 U.S.C. 154(b) by 1484 days.

(21) Appl. No.: 12/090,215

(22) PCT Filed: Oct. 11, 2006

(86) PCT No.: PCT/ES2006/070152
§ 371 (c)(1),
(2), (4) Date: Sep. 25, 2008

(87) PCT Pub. No.: WO2007/090911
PCT Pub. Date: Aug. 16, 2007

(65) Prior Publication Data
US 2009/0202503 A1 Aug. 13, 2009

(30) Foreign Application Priority Data
Oct. 14, 2005 (ES) .................................. 200502511

(51) Int. Cl.
*A61K 38/00* (2006.01)
*A61K 38/04* (2006.01)
*A61K 38/10* (2006.01)
*A61K 38/16* (2006.01)
*C12N 9/12* (2006.01)

(52) U.S. Cl.
CPC ............... *C12N 9/1241* (2013.01); *A61K 38/00* (2013.01)

(58) Field of Classification Search
CPC ....... A61K 38/00; A61K 38/04; A61K 38/10; A61K 38/16
USPC ............... 530/300, 324, 326; 514/2
See application file for complete search history.

(56) References Cited

U.S. PATENT DOCUMENTS 5,350,836 A * 9/1994 Kopchick et al. ............. 530/399

FOREIGN PATENT DOCUMENTS

WO WO-9954449 10/1999

OTHER PUBLICATIONS

GenBank Accession NP_596910; dated Mar. 6, 2002.*
Bowie et al, Science 257:1306-1310, 1990.*
Wells, Biochemistry 29:8509-8517, 1990.*
Ngo et al., The Protein Folding Problem and Tertiary Structure Prediction, pp. 492-495, 1994.*
Vukicevic et al, PNAS USA 93:9021-9026, 1996.*
Youssoufian et al, Blood Cells, Molecules and Diseases 25(20):305-309, 1999.*
Bessler et al., "Dyskeratosis congenita and telomerase", Curr Opin Pediatr 2004: 16(1):23-8.
Cheng at al., "Inhibition on telomerase activity and cytotoxic effects by cisplatin in cultured human choroidal melanoma cells", *Yan Ke Xue Bao* 2003;19(1):54-9.
Marrone and Mason, "Dyskeratosis congenita", Cell Mol Life 2003; 60(3):507-517.
Mese et al., "Inhibition of telomerase activity as a measure of tumor cell killing by cisplatin in squamous cell carcinoma cell line", *Chemotherapy* 2001; 47(2):136-42.
Poole et al., "Activity, function, and gene regulation of the catalytic subunit of telomerase (hTERT)", *Gene* 2001; 16: 269(1-2):1-12.
Siddiqui-Jain et al. "Direct evidence for a G-quadruplex in a promoter region and its targeting with a small molecule to repress c-MYC transcription", *Proc Natl Acad Sci USA* 2002; 3; 99(18):11593-8.
Trowbridge et al., "Dyskeratosis congenita: hematologic evaluation of a sibship and review of the literature", *Am. J. Hematol* 1977; 3:143-152.
Zhang et al., "Effects of cisplatin on telomerase activity and telomere length in BEL-7404 human hepatoma cells", *Cell Res* 2002; 12(1):55-62.
Zucchini et al., "The human TruB family of pseudouridine synthase genes, including the Dyskeratosis Congenita 1 gene and the novel member TRUB1", *Int J Mol Med* 2003; 11(6):697-704.

(Continued)

*Primary Examiner* — Kevin Hill
(74) *Attorney, Agent, or Firm* — Leason Ellis LLP

(57) ABSTRACT

This invention relates to a compound that induces or activates telomerase activity based on the nucleotide sequence of the GSE 24.2 fragment of dyskerin or the protein or peptide sequence encoded by said nucleotide sequence. Another part of the invention relates to vectors that comprise said sequence and cells transformed thereby, and pharmaceutical compositions that contain all these elements. These compositions may be used in the treatment of diseases from the following group: ageing or acceleration of ageing, neurodegenerative diseases and dyskeratosis congenita.

8 Claims, 11 Drawing Sheets

(56) References Cited

OTHER PUBLICATIONS

Vulliamy et al., "Dyskeratosis caused by a 3' deletion: Germline and somatic mosaicism in a female carrier", *Blood* 1999; 94:1254-1260.
Kim et al., "Identification of a quinoxaline derivative that is a potent telomerase inhibitor leading to cellular senescence of human cancer cells", Biochem J 2003; 15; 373 (Pt 2):523-9.
Harlow and Lane, "Using antibodies: a laboratory manual", Cold Spring Harbor Laboratory Press 1999; Tagging Proteins:347-377.
Sambrook et al., "Molecular cloning, a Laboratory Manual, Second Edition", Cold Spring Harbor Laboratory Press 1989; pp. 1.54-1.73 and pp. 16.30-16.40.
Bednarek et al., "Supression of cell proliferation and telomerase activity in 4-(hydroxyphenyl)retinamide-treated mammary tumors", *Carcinogenesis* 1999; 20(5):879.
Burger et al., "Inhibition of Telomerase Activity by Cisplatin in Human Testicular Cancer Cells", *Eur J Cancer* 1997; 33(4):638-44.
Cesare and Griffith, "Telomeric DNA in ALT cells is characterized by free telomeric circles and heterogeneous t-loops", *Mol. Cell. Biol.* 2004; 24(22):9948-9957.
Fu and Collins, "Distinct biogenesis pathways for human telomerase RNA and H/ACA small nucleolar RNAs", *Mol Cell* 2003; 11(5):1361-72.
Grand et al., "Mutations in the G-quadruplex silencer element and their relationship to c-MYC overexpression, NM23 repression, and therapeutic rescue", *Proc Natl Acad Sci USA* 2004; 101(16):6140-6145.
Heiss et al., X-linked dyskeratosis congenita is caused by mutations in a highly conserved gene with putative nucleolar functions, *Nat Genet* 1998; 19(1):32-8.
Ishibashi and Lippard, "Telomere loss in cells treated with cisplatin" *Proc Natl Acad Sci USA* 1998; 95(8):4219-23.
Lemarteleur et al., "Stabilization of the c-myc gene promoter quadruplex by specific ligands' inhibitors of telomerase", *Biochem Biphys Res Commun* 2004; 22; 323(3): 802-8.
Mitchell et al., "A telomerase component is defective in the human disease dyskeratosis congenita", *Nature* 1999; 402(6761):551-5.
Mochizuki et al., "Mouse dyskerin mutations affect accumulation of telomerase RNA and small nucleolar RNA, telomerase activity, and ribosomal RNA processing", *Proc Natl Acad Sci USA* 2004; 101(29):10756-61.
Oh et al., "In vivo and in vitro analyses of Myc for differential promoter activities of the human telomerase (hTERT) gene in normal and tumor cells", *Biochem Biophys Res Commun* 1999; 263(2):361-5.
Pan et al., "Structure of tRNA pseudouridine synthase TruB and its RNA complex: RNA recognition through a combination of rigid docking and induced fit", *Proc Natl Acad Sci USA* 2003; 100(22):2648-53.
Redon and Elizondo-Riojas, "Platination of the (T2G4)4 telomeric sequence: a structural and corss-linking study", *Biochemistry* 2001; 24; 40(29): 8463-70.
Roninson et al., "Genetic suppressor elements: new tools for molecular oncology", *Cancer Res* 1995; 15; 55(18):4023-8.
Sanchez-Perez et al., "Cisplatin induces a persistent activation of JNK that is related to cell death", Oncogene 1998; 29; 16(4):533-40.
Sirnavin and Trowbridge, "Dyskeratosis congenita: clinical features and genetic aspects", *J. Med. Genet.* 1975; 12:339-354.
Sun et al., "Inhibition of human telomerase by a G-quadruplex-interactive compound" *J Med Chem* 1997; 4; 40(14):2113-6.
Wright et al., "Modifications of a telomeric repeat amplification protocol (TRAP) result in increased reliability, linearity and sensitivity", *Nucleic Acids Res* 1995; 25; 23(18):3794-5.
Yoshiro et al., "Tumor metastasis supressor nm23H1 regulates Rac1 G interaction with Tiam1", *Proc Natl Acad Sci USA* 2001; 98(8):4385-4390.
Gowan et al., "A G-quadruplex-interactive potent small-molecule inhibitor of telomerase exhibiting in vitro and in vivo antitumer activity", *Mol Pharmacol* 2002; 61:1154-1162.
Kim et al., "The Wilms' tumor 1 tumor suppressor Gene Represses Transcription of the Human Telomerase Reverse Transcription Gene" the Journal of Biological Chemistry 1999 pp. 37473-37478.
Wu, et al. "Direct activation iof TERT transcription by c-MYC" Nature Genetice, vol. 21, Feb. 1999. pp. 220-224.

\* cited by examiner

A)

B)

SEQUENCE LISTING

```
<160> NUMBER OF SEQ ID NOS: 24

<210> SEQ ID NO 1
<211> LENGTH: 165
<212> TYPE: DNA
<213> ORGANISM: Homo sapiens
<220> FEATURE:
<221> NAME/KEY: CDS
<222> LOCATION: (1)..(165)
<223> OTHER INFORMATION: Sequence GSE 24.2

<400> SEQUENCE: 1 ggt ttc att aat ctt gac aag ccc tct aac ccc tct tcc cat gag gtg     48
Gly Phe Ile Asn Leu Asp Lys Pro Ser Asn Pro Ser Ser His Glu Val
1               5                  10                  15 gta gcc tgg att cga cgg ata ctt cgg gtg gag aag aca ggg cac agt     96
Val Ala Trp Ile Arg Arg Ile Leu Arg Val Glu Lys Thr Gly His Ser
            20                  25                  30 ggt act ctg gat ccc aag gtg act ggt tgt tta atc gtg tgc ata gaa    144
```

```
Gly Thr Leu Asp Pro Lys Val Thr Gly Cys Leu Ile Val Cys Ile Glu
         35                  40                  45 cga gcc act cgc ttg gtg aag                                          165
Arg Ala Thr Arg Leu Val Lys
 50                  55

<210> SEQ ID NO 2
<211> LENGTH: 55
<212> TYPE: PRT
<213> ORGANISM: Homo sapiens

<400> SEQUENCE: 2

Gly Phe Ile Asn Leu Asp Lys Pro Ser Asn Pro Ser His Glu Val
 1               5                  10                  15

Val Ala Trp Ile Arg Arg Ile Leu Arg Val Glu Lys Thr Gly His Ser
             20                  25                  30

Gly Thr Leu Asp Pro Lys Val Thr Gly Cys Leu Ile Val Cys Ile Glu
         35                  40                  45

Arg Ala Thr Arg Leu Val Lys
 50                  55

<210> SEQ ID NO 3
<211> LENGTH: 496
<212> TYPE: DNA
<213> ORGANISM: Homo sapiens
<220> FEATURE:
<221> NAME/KEY: CDS
<222> LOCATION: (1)..(495)

<400> SEQUENCE: 3 atg gcg gat gcg gaa gta att att ttg cca aag aaa cat aag aag aaa    48
Met Ala Asp Ala Glu Val Ile Ile Leu Pro Lys Lys His Lys Lys Lys
 1               5                  10                  15 aag gag cgg aag tca ttg cca gaa gaa gat gta gcc gaa ata caa cac    96
Lys Glu Arg Lys Ser Leu Pro Glu Glu Asp Val Ala Glu Ile Gln His
             20                  25                  30 gct gaa gaa ttt ctt atc aaa cct gaa tcc aaa gtt gct aag ttg gac   144
Ala Glu Glu Phe Leu Ile Lys Pro Glu Ser Lys Val Ala Lys Leu Asp
         35                  40                  45 acg tct cag tgg ccc ctt ttg cta aag aat ttt gat aag ctg aat gta   192
Thr Ser Gln Trp Pro Leu Leu Leu Lys Asn Phe Asp Lys Leu Asn Val
 50                  55                  60 agg aca aca cac tat aca cct ctt gca tgt ggt tca aat cct ctg aag   240
Arg Thr Thr His Tyr Thr Pro Leu Ala Cys Gly Ser Asn Pro Leu Lys
 65                  70                  75                  80 aga gag att ggg gac tat atc agg aca ggt ttc att aat ctt gac aag   288
Arg Glu Ile Gly Asp Tyr Ile Arg Thr Gly Phe Ile Asn Leu Asp Lys
             85                  90                  95 ccc tct aac ccc tct tcc cat gag gtg gta gcc tgg att cga cgg ata   336
Pro Ser Asn Pro Ser Ser His Glu Val Val Ala Trp Ile Arg Arg Ile
        100                 105                 110 ctt cgg gtg gag aag aca ggg cac agt ggt act ctg gat ccc aag gtg   384
Leu Arg Val Glu Lys Thr Gly His Ser Gly Thr Leu Asp Pro Lys Val
            115                 120                 125 act ggt tgt tta atc gtg tgc ata gaa cga gcc act cgc ttg gtg aag   432
Thr Gly Cys Leu Ile Val Cys Ile Glu Arg Ala Thr Arg Leu Val Lys
        130                 135                 140 tca caa cag agt gca ggc aaa gag tat gtg ggg att gtc cgg ctg cac   480
Ser Gln Gln Ser Ala Gly Lys Glu Tyr Val Gly Ile Val Arg Leu His
145                 150                 155                 160 aat gct att gaa ggg g                                             496
```

```
Asn Ala Ile Glu Gly
            165

<210> SEQ ID NO 4
<211> LENGTH: 165
<212> TYPE: PRT
<213> ORGANISM: Homo sapiens

<400> SEQUENCE: 4

Met Ala Asp Ala Glu Val Ile Ile Leu Pro Lys Lys His Lys Lys Lys
1               5                   10                  15

Lys Glu Arg Lys Ser Leu Pro Glu Asp Val Ala Glu Ile Gln His
            20                  25                  30

Ala Glu Glu Phe Leu Ile Lys Pro Glu Ser Lys Val Ala Lys Leu Asp
            35                  40                  45

Thr Ser Gln Trp Pro Leu Leu Leu Lys Asn Phe Asp Lys Leu Asn Val
        50                  55                  60

Arg Thr Thr His Tyr Thr Pro Leu Ala Cys Gly Ser Asn Pro Leu Lys
65                  70                  75                  80

Arg Glu Ile Gly Asp Tyr Ile Arg Thr Gly Phe Ile Asn Leu Asp Lys
                85                  90                  95

Pro Ser Asn Pro Ser Ser His Glu Val Val Ala Trp Ile Arg Arg Ile
            100                 105                 110

Leu Arg Val Glu Lys Thr Gly His Ser Gly Thr Leu Asp Pro Lys Val
            115                 120                 125

Thr Gly Cys Leu Ile Val Cys Ile Glu Arg Ala Thr Arg Leu Val Lys
        130                 135                 140

Ser Gln Gln Ser Ala Gly Lys Glu Tyr Val Gly Ile Val Arg Leu His
145                 150                 155                 160

Asn Ala Ile Glu Gly
            165

<210> SEQ ID NO 5
<211> LENGTH: 20
<212> TYPE: DNA
<213> ORGANISM: Artificial sequence
<220> FEATURE:
<223> OTHER INFORMATION: Oligo A for hTERT

<400> SEQUENCE: 5
cggaagagtg tctggagcaa                                                 20

<210> SEQ ID NO 6
<211> LENGTH: 18
<212> TYPE: DNA
<213> ORGANISM: Artificial sequence
<220> FEATURE:
<223> OTHER INFORMATION: Oligo B for hTERT

<400> SEQUENCE: 6
ggatgaagcg gagtcgga                                                   18

<210> SEQ ID NO 7
<211> LENGTH: 26
<212> TYPE: DNA
<213> ORGANISM: Artificial sequence
<220> FEATURE:
<223> OTHER INFORMATION: Oligo C for hTR

<400> SEQUENCE: 7 tctaaccctaactgagaaggg gcgtag                                          26
```

<210> SEQ ID NO 8
<211> LENGTH: 26
<212> TYPE: DNA
<213> ORGANISM: Artificial sequence
<220> FEATURE:
<223> OTHER INFORMATION: Oligo D for hTR

<400> SEQUENCE: 8
gtttgctcta gaatgaacgg tggaag                                         26

<210> SEQ ID NO 9
<211> LENGTH: 21
<212> TYPE: DNA
<213> ORGANISM: Artificial sequence
<220> FEATURE:
<223> OTHER INFORMATION: Oligo E for dyskerin

<400> SEQUENCE: 9
atggcggatg cggaagtaat t                                              21

<210> SEQ ID NO 10
<211> LENGTH: 20
<212> TYPE: DNA
<213> ORGANISM: Artificial sequence
<220> FEATURE:
<223> OTHER INFORMATION: Oligo F for dyskerin

<400> SEQUENCE: 10 cccctttcaat agcattgtgc                                               20

<210> SEQ ID NO 11
<211> LENGTH: 54
<212> TYPE: DNA
<213> ORGANISM: Homo sapiens
<220> FEATURE:
<221> NAME/KEY: CDS
<222> LOCATION: (1)..(54)
<220> FEATURE:
<221> NAME/KEY: misc_feature
<222> LOCATION: (4)..(50)
<223> OTHER INFORMATION: TrubI dominion

<400> SEQUENCE: 11 ggt ttc att aat ctt gac aag ccc tct aac ccc tct tcc cat gag gtg    48
Gly Phe Ile Asn Leu Asp Lys Pro Ser Asn Pro Ser Ser His Glu Val
 1               5                  10                  15 gta gcc                                                              54
Val Ala

<210> SEQ ID NO 12
<211> LENGTH: 18
<212> TYPE: PRT
<213> ORGANISM: Homo sapiens

<400> SEQUENCE: 12

Gly Phe Ile Asn Leu Asp Lys Pro Ser Asn Pro Ser Ser His Glu Val
 1               5                  10                  15

Val Ala

<210> SEQ ID NO 13
<211> LENGTH: 75
<212> TYPE: DNA
<213> ORGANISM: Homo sapiens
<220> FEATURE:
<221> NAME/KEY: CDS

```
<222> LOCATION: (1)..(75)
<220> FEATURE:
<221> NAME/KEY: misc_feature
<222> LOCATION: (4)..(50)
<223> OTHER INFORMATION: Trub II dominion

<400> SEQUENCE: 13 cac agt ggt act ctg gat ccc aag gtg act ggt tgt tta atc gtg tgc      48
His Ser Gly Thr Leu Asp Pro Lys Val Thr Gly Cys Leu Ile Val Cys
1               5                   10                  15 ata gaa cga gcc act cgc ttg gtg aag                                  75
Ile Glu Arg Ala Thr Arg Leu Val Lys
                20                  25

<210> SEQ ID NO 14
<211> LENGTH: 25
<212> TYPE: PRT
<213> ORGANISM: Homo sapiens

<400> SEQUENCE: 14

His Ser Gly Thr Leu Asp Pro Lys Val Thr Gly Cys Leu Ile Val Cys
1               5                   10                  15

Ile Glu Arg Ala Thr Arg Leu Val Lys
                20                  25

<210> SEQ ID NO 15
<211> LENGTH: 54
<212> TYPE: PRT
<213> ORGANISM: Homo sapiens

<400> SEQUENCE: 15

Gly Phe Ile Asn Leu Asp Lys Pro Ser Asn Pro Ser Ser His Glu Val
1               5                   10                  15

Val Ala Trp Ile Arg Arg Ile Leu Arg Val Glu Lys Thr Gly His Ser
                20                  25                  30

Gly Thr Leu Asp Pro Lys Val Thr Gly Cys Leu Ile Val Cys Ile Glu
            35                  40                  45

Arg Ala Thr Arg Leu Val
        50

<210> SEQ ID NO 16
<211> LENGTH: 54
<212> TYPE: PRT
<213> ORGANISM: Mus musculus

<400> SEQUENCE: 16

Gly Phe Ile Asn Leu Asp Lys Pro Ser Asn Pro Ser Ser His Glu Val
1               5                   10                  15

Val Ala Trp Ile Arg Arg Ile Leu Arg Val Glu Lys Thr Gly His Ser
                20                  25                  30

Gly Thr Leu Asp Pro Lys Val Thr Gly Cys Leu Ile Val Cys Ile Glu
            35                  40                  45

Arg Ala Thr Arg Leu Val
        50

<210> SEQ ID NO 17
<211> LENGTH: 54
<212> TYPE: PRT
<213> ORGANISM: Rattus norvegicus

<400> SEQUENCE: 17

Gly Phe Ile Asn Leu Asp Lys Pro Ser Asn Pro Ser Ser His Glu Val
```

```
                1               5                  10                 15
Val Ala Trp Ile Arg Arg Ile Leu Arg Val Glu Lys Thr Gly His Ser
                20                      25                 30
Gly Thr Leu Asp Pro Lys Val Thr Gly Cys Leu Ile Val Cys Ile Glu
        35                      40                 45
Arg Ala Thr Arg Leu Val
        50
```

<210> SEQ ID NO 18
<211> LENGTH: 54
<212> TYPE: PRT
<213> ORGANISM: Drosophila melanogaster

<400> SEQUENCE: 18

```
Gly Phe Ile Asn Leu Asp Lys Pro Ser Asn Pro Ser His Glu Val
1               5                      10                 15
Val Ala Trp Ile Lys Lys Ile Leu Lys Val Glu Lys Thr Gly His Ser
                20                      25                 30
Gly Thr Leu Asp Pro Lys Val Thr Gly Cys Leu Ile Val Cys Ile Asp
        35                      40                 45
Arg Ala Thr Arg Leu Val
        50
```

<210> SEQ ID NO 19
<211> LENGTH: 54
<212> TYPE: PRT
<213> ORGANISM: Danio rerio

<400> SEQUENCE: 19

```
Gly Phe Ile Asn Leu Asp Lys Pro Ala Asn Pro Ser His Glu Val
1               5                      10                 15
Val Ala Trp Ile Lys Arg Ile Leu Arg Val Glu Lys Thr Gly His Ser
                20                      25                 30
Gly Thr Leu Asp Pro Lys Val Thr Gly Cys Leu Ile Val Tyr Val Glu
        35                      40                 45
Arg Ala Thr Arg Leu Val
        50
```

<210> SEQ ID NO 20
<211> LENGTH: 54
<212> TYPE: PRT
<213> ORGANISM: Saccharomyces cerevisiae

<400> SEQUENCE: 20

```
Gly Val Ile Asn Leu Asp Lys Pro Ser Asn Pro Ser His Glu Val
1               5                      10                 15
Val Ala Trp Ile Lys Arg Ile Leu Arg Cys Glu Lys Thr Gly His Ser
                20                      25                 30
Gly Thr Leu Asp Pro Lys Val Thr Gly Cys Leu Ile Val Cys Ile Asp
        35                      40                 45
Arg Ala Thr Arg Leu Val
        50
```

<210> SEQ ID NO 21
<211> LENGTH: 27
<212> TYPE: DNA
<213> ORGANISM: Artificial Sequence
<220> FEATURE:
<223> OTHER INFORMATION: px3.2

```
<400> SEQUENCE: 21
tggggagggt ggggagggtg gggaagg                                              27

<210> SEQ ID NO 22
<211> LENGTH: 27
<212> TYPE: DNA
<213> ORGANISM: Artificial Sequence
<220> FEATURE:
<223> OTHER INFORMATION: px3.2 G12A

<400> SEQUENCE: 22
tggggagggt gaggagggtg gggaagg                                              27

<210> SEQ ID NO 23
<211> LENGTH: 27
<212> TYPE: DNA
<213> ORGANISM: Artificial Sequence
<220> FEATURE:
<223> OTHER INFORMATION: px3.2 G17A

<400> SEQUENCE: 23
tggggagggt ggggagagtg gggaagg                                              27

<210> SEQ ID NO 24
<211> LENGTH: 27
<212> TYPE: DNA
<213> ORGANISM: Artificial Sequence
<220> FEATURE:
<223> OTHER INFORMATION: px3.2 G26T/G27T

<400> SEQUENCE: 24
tggggagggt ggggagggtg gggaatt                                              27
```

SEQUENCE OF NUCLEOTIDES AND PEPTIDES GSE 24.2 OF DYSKERIN, WHICH CAN INDUCE TELOMERASE ACTIVITY, METHOD FOR OBTAINING SAME, THERAPEUTIC COMPOSITIONS AND APPLICATIONS THEREOF

This application is a U.S. national phase application under 35 U.S.C. §371 of International Patent Application No. PCT/ES2006/070152 filed Oct. 11, 2006, which claims the benefit of priority to the Spanish Application No. P200502511 filed Oct. 14, 2005, the disclosures of all of which are hereby incorporated by reference in their entireties. The International Application was published in Spanish on Aug. 16, 2007 as WO 2007/090911.

FIELD OF THE INVENTION

The present invention relates to a biotechnological sector with applications related to human health and, more specifically, biological compounds—nucleotide sequences, peptides and transformed human cells—with therapeutic applications for human beings.

BACKGROUND

Dyskerin (FIG. 1) is a 58-kD nucleolar protein that is associated with the H/ACA box SnoRNAs, present in the small ribonucleoprotein particles in charge of pseudouridylation modification of ribosomal RNA. On the other hand, it is also a component of the telomerase complex, which is responsible for maintaining telomeric repetitions at the chromosome ends. The X-chromosome-linked form of dyskeratosis congenita (DC) (Marrone et al., 2003; Besseler et al., 2004) is a congenital syndrome that causes bone marrow failure and is associated with greater susceptibility to cancer. This form of dyskeratosis is caused by a specific mutation of the DKC1 gene, which encodes dyskerin. There also exists an autosomal dominant dyskeratosis congenita; in this case, the disease is associated with mutations in the RNA component of telomerase (hTR) (Heiss et al., 1998). In the fibroblasts and lymphoblasts of patients with dyskeratosis congenita there is less telomerase activity, and the telomeres are shorter than those of cells not affected by the disease (Siriniavin et al., 1975; Trowbridge et al., 1977). In the cells of patients with the X-chromosome-linked form of dyskeratosis congenita, telomerase defects have been overcome by expressing the reverse transcriptase catalytic subunit (hTERT) ectopically (Mitchell et al., 1999). In dyskeratosis congenita caused by mutations in hTR, the only way to recover telomerase activity is by re-expressing hTR (Fu et al., 2003).

Telomeres are composed of 500-2,000 repetitions of the TTAGGG conserved sequence at the chromosome 3' end and their shortening through successive divisions becomes a limitation for the cell's proliferation capacity. Telomeres are susceptible to suffering DNA damage caused by exogenous agents, including cisplatin. It has been described that cisplatin is capable of inhibiting telomerase activity in different cell lines (Ishibashi et al., 1998; Burger et al., 1997). There are several hypotheses as to how this inhibition may occur. One possibility is the formation of G-Pt-G adducts, typical of cisplatin, in the repeated sequence of TTAGGG telomeres. Alternatively, interactions of cisplatin with sulfhydryl groups essential for the reverse transcriptase catalytic subunit (hTERT) and it could even be due to the reduction in hTERT expression (Burger et al., 1997).

SUMMARY OF THE INVENTION

One embodiment of the invention is a pharmaceutical compound that induces or activates telomerase activity, hereinafter termed activator compound, based on the nucleotide sequence of the Gene suppression elements (GSE) 24.2 fragment of dyskerin or the protein or peptide sequence encoded by said nucleotide sequence which is capable of recovering telomerase activity in the interior of the cells of a mammal, preferably human.

One particular embodiment of the invention is a nucleotide sequence, hereinafter GSE 24.2 gene sequence of this invention, which allows for the expression of a protein or peptide that induces telomerase activity in the interior of the cells of a mammal, preferably human, and which consists of one or several GSE 24.2 nucleotide sequences belonging to the following group:
  a) a nucleotide sequence composed of a human GSE 24.2 nucleotide sequence (SEQ ID NO1),
  b) a nucleotide sequence analogous to the sequence of a),
  c) a fragment of any of sequences a) and b), and
  d) a nucleotide sequence, genetic construct, that comprises any sequence belonging to a), b) and c).

As used in this invention, the term "nucleotide sequence" refers to a DNA, cDNA or mRNA sequence.

A particular embodiment of this invention is the nucleotide sequence of the GSE 24.2 sequence of a) composed of SEQ ID NO1.

Another particular embodiment of this invention is the nucleotide sequence of the GSE 24.2 sequence of b) composed of SEQ ID NO11 or SEQ ID NO13, which encode the Trub I and Trub II peptide domains, respectively (Example 1.7).

Another particular embodiment of this invention is a GSE 24.2 genetic construct which comprises the GSE 24.2 nucleotide sequence.

Another particular embodiment of this invention is a GSE 24.2 expression vector which comprises a GSE 24.2 nucleotide sequence or a GSE 24.2 genetic construct, described in this invention, and which allows for the expression of a protein or peptide capable of recovering telomerase activity in the interior of the cells of mammals, preferably humans. One example of this particular embodiment is the pLNCX 24.2 expression vector of the invention (see examples).

In addition, another particular embodiment of the invention is a protein or peptide, hereinafter GSE 24.2 protein of this invention, which exhibits activity aimed at recovering telomerase in the interior of the cells of a mammal, preferably human, and which comprises one or several amino acid sequences belonging to the following group:
  a) an amino acid sequence composed of a human GSE 24.2 amino acid sequence (SEQ ID NO2),
  b) an amino acid sequence analogous to the sequence of a),
  c) a fragment of any of the sequences of a) and b), and
  d) an amino acid sequence that comprises any sequence belonging to a), b) and c).

Another particular embodiment of this invention is a protein whose amino acid sequence of a) is composed of SEQ ID NO2.

Another particular embodiment of this invention is a protein whose amino acid sequence of c), fragment of which is composed of SEQ ID NO12 or SEQ ID NO14.

On the other hand, an additional embodiment of this invention comprises genetically modified cells, either eukaryotic—preferably human—or prokaryotic, hereinafter GSE 24.2 cells of the invention, which comprise the GSE 24.2 nucleotide sequence, construct, and expression vector of the invention, and wherein the GSE 24.2 peptide or protein of the invention may be adequately expressed.

Therefore, another embodiment of the invention is the use of the GSE 24.2 activator compound of this invention in the preparation of a drug or pharmaceutical composition for the treatment of a disease caused by an alteration of, preferably a reduction in, telomerase activity, belonging, for illustrative purposes and without this limiting the scope of the invention, to the following group: ageing or acceleration of ageing, neurodegenerative diseases, and dyskeratosis congenita.

Another embodiment of this invention is a pharmaceutical composition or drug for the treatment of diseases, disorders, or pathologies that develop with alterations of telomerase activity, preferably a reduction in activity, hereinafter pharmaceutical composition of this invention, which comprises a therapeutically effective quantity of a compound or agent capable of recovering telomerase activity jointly with, optionally, one or more pharmaceutically acceptable adjuvants and/or vehicles, and which is capable of stimulating the generation and maintenance of telomerase activity.

Another particular embodiment of this invention is a pharmaceutical composition of the invention wherein the compound or agent capable of recovering telomerase activity belongs to the following group: GSE 24.2 sequence, genetic construct, or vector that allow for the expression of a protein or peptide capable of recovering telomerase activity in the interior of the cells of a mammal, preferably human.

A particular embodiment of the invention is a pharmaceutical composition of the invention wherein the compound or agent capable of recovering telomerase activity is one or several GSE 24.2 sequences belonging to the following group:
 a) a nucleotide sequence composed of a human GSE 24.2 nucleotide sequence (SEQ ID NO1),
 b) a nucleotide sequence analogous to the sequence of a),
 c) a fragment of any of the sequences of a) and b), and
 d) a nucleotide sequence, genetic construct, that comprises any sequence belonging to a), b) and c).

Another particular embodiment of this invention is the pharmaceutical composition of the invention wherein the nucleotide sequence of a) is the GSE 24.2 nucleotide sequence (SEQ ID NO1).

Another particular embodiment of this invention is the pharmaceutical composition of the invention wherein the nucleotide sequence of c) is the SEQ ID NO11 or SEQ ID NO 13 nucleotide sequence.

Another particular embodiment of this invention is a pharmaceutical composition of the invention wherein the nucleotide sequence is a vector, preferably the pLNCX 24.2 vector.

Another particular embodiment of this invention is a pharmaceutical composition of the invention wherein the compound or agent capable of recovering telomerase activity is a protein or a peptide encoded by the GSE 24.2 sequence, genetic construct or vector of the invention.

A particular embodiment of the invention is a pharmaceutical composition of the invention wherein the GSE 24.2 protein or peptide belongs to the following group:
 a) an amino acid sequence composed of a human GSE 24.2 amino acid sequence (SEQ ID NO2),
 b) an amino acid sequence analogous to the sequence of a),
 c) a fragment of any of the sequences of a) and b), and
 d) an amino acid sequence that comprises any sequence belonging to a), b) and c).

Another particular embodiment of this invention is the pharmaceutical composition of the invention wherein the amino acid sequence of a) is the SEQ ID NO2 sequence.

Another particular embodiment of this invention is the pharmaceutical composition of the invention wherein the amino acid sequence of c) is the SEQ ID NO12 or SEQ ID NO14 sequence.

Another particular embodiment of this invention is a pharmaceutical composition of the invention wherein the telomerase-activating compound or agent is a cell, preferably human, transformed by the GSE 24.2 sequence, construct or vector.

Another embodiment of the invention is the use of the pharmaceutical composition of the invention, hereinafter use of the pharmaceutical composition of the invention, in a method of treatment or prophylaxis for a mammal, preferably a human being, affected by a disease, disorder, or pathology that develops with alterations of telomerase activity, consisting of the administration of said therapeutic composition in a suitable dose which allows for the recovery of telomerase activity in the interior of its cells.

Another particular embodiment of this invention is the use of the pharmaceutical composition of the invention in a treatment method for a disease or disorder that develops with alterations of telomerase activity and which affects human beings, belonging, for illustrative purposes and without this limiting the scope of the invention, to the following group: ageing or acceleration of ageing, neurodegenerative diseases, dyskeratosis congenita, Cri du chat, ataxia telangiectasia, Nijmegen Breakage Syndrome, Bloom Syndrome, Werner Syndrome, Fanconi's anaemia, ulcerous colitis, vascular ageing, atherosclerosis, and cancer.

Another particular embodiment of this invention is the use of the pharmaceutical composition of the invention in a treatment method for a neurodegenerative disease belonging to the following group: Alzheimer's disease, Parkinson's disease, cerebellar ataxia and spinal cord degeneration.

Another particular embodiment of this invention is the use of the pharmaceutical composition of the invention in a treatment method for the X-chromosome-linked form of dyskeratosis congenita.

Another particular embodiment of this invention is the use of the pharmaceutical composition of the invention in a treatment method for autosomal dominant dyskeratosis congenita.

DETAILED DESCRIPTION

This invention addresses the problem of providing new therapeutic tools for the treatment of diseases that develop with alterations of telomerase activity and, more specifically, dyskeratosis congenita.

This invention is based on the fact that the inventors have proven that the expression of a cDNA fragment of dyskerin, fragment GSE 24.2 (SEQ ID NO1), which expresses an internal sequence of dyskerin (SEQ ID NO2), compensates for the defects in telomerase activity in the cells of patients with dyskeratosis congenita and in VA13 cells (Example 3). More specifically, when the cells of patients with dyskeratosis congenita and VA13 cells are transfected with the GSE 24.2 sequence, in addition to recovering telomerase activity, there is an increase in hTERT and hTR levels. In fact, it was observed that the expression of the GSE 24.2 peptide increased the baseline activity of the telomerase promoter and, following treatment with cisplatin, the GSE 24.2 cells also had greater activity. Curiously, Collins et al. had previously described that, in the cells of these same patients, telomerase activity was only recovered by overexpressing the hTERT gene, and not by expressing dyskerin, a protein which is mutated in these patients (Mitchell et al., 1999).

It has been described in the literature that mutations in dyskerin could affect the accumulation of the telomerase RNA (Mochizuki et al., 2004); therefore, the effects caused by the GSE 24.2 peptide could be due to an increase in hTERT levels and a greater stabilisation of hTR, since the increase in hTERT levels could stabilise the formation of the telomerase complex, thereby preventing the degradation of hTR. In this regard, in this invention it has been observed that, in cells transfected with the GSE 24.2 peptide, the hTERT protein promoter, but not hTR, is constitutively activated in a manner dependent on c-myc expression, more specifically through its binding to the NHEIII region, located in the purine-rich P1 region of the promoter (Pu27, see Example 2), thus allowing for a change in the secondary conformation of DNA, in such a way that transcription factors may access the DNA. Any change in the sequence of this region that modifies the secondary structure thereof alters the activity of the GSE 24.2 peptide.

Similarly, a sequence equivalent to the human GSE 24.2 peptide (CBF5 of yeast, *S. cerevisiae* CBF5) exhibits a similar activity in the activation of hTERT (data not shown), indicating a high degree of functional conservation in the activity of this domain of dyskerin, thus defining and illustrating the multiple possibilities of elements or sequences homologous to GSE 24.2 that may be used in this invention.

Moreover, this GSE 24.2 peptide provides human cell lines with a survival capacity to cisplatin (Example 1). The GSE 24.2 cell line increases viability in the face of the inhibitor of telomerase 1. This inhibitor has an action mechanism that is similar to cisplatin, forming G-quadruplexes in the telomeres and reducing telomerase activity (Sun et al., 1997). Sequences have also been described which form G-quadruplexes in an hTERT intron; therefore, it is possible that this inhibitor also reduces hTERT levels, thereby also reducing telomerase activity (Lemateleur et al., 2004).

Bearing in mind that both cisplatin and the inhibitor of telomerase stabilise the formation of G-quadruplexes (Redon et al., 2001), which could in turn block telomerase activity, the GSE 24.2 peptide could reduce the efficacy of these inhibitors by preventing or reducing the formation of these G-quadruplexes, or perhaps it is capable of increasing hTERT levels, thus increasing telomerase activity, through another mechanism.

Gene suppression elements (GSEs) are biologically active cDNA fragments that encode peptides or RNA anti-sense inhibitors and act in a dominant fashion on gene expression in mammal cells. GSE 24.2 is a 165-pb fragment that comprises nucleotides 268 to 433, and corresponds to a sequence formed by two highly conserved domains in different species, called TRUB (FIG. 2b, see SEQ ID NO12 and 14, respectively). These domains seem to have an important function in the pseudouridinisation of snoRNAs (Zucchini et al., 2003; Pan et al., 2003) and, what is more surprising, nucleotide sequences prepared with such domains, separately cloned, increased the baseline activity of the telomerase promoter like the initially described, entire sequence of 55 amino acids (Example 1.7, FIG. 8c). It is interesting to note that this activity, which induces resistance to cisplatin and compensates for defects in telomerase activity, is only located in the region of dyskerin found in the GSE 24.2 sequence, since the complete protein (see SEQ ID 4) or the aminoterminal fragment do not have any activity whatsoever. These results open new therapeutic prospects for human disorders or diseases caused by alterations of the telomerase complex (shortening of telomeres and diseases with cell ageing or stem cells), such that the GSE 24.2 element or derivatives thereof may be used as drugs to recover telomerase activity. Moreover, there are different syndromes other than DC, which include a shortening of telomeres among other cellular phenotypes, and also bone marrow failures, immunosuppression, and predisposition to cancer. The telomerase gene is not affected by mutations in GSEs, but telomere replacement and telomerase activity are.

Therefore, one embodiment of this invention is a compound that induces or activates telomerase activity, hereinafter activator compound of this invention, based on the nucleotide sequence of the GSE 24.2 fragment of dyskerin, or the protein or peptide sequence encoded by said nucleotide sequence, which is capable of recovering telomerase activity in the interior of the cells of a mammal, preferably human.

As used in this invention, the term "compound that induces or activates telomerase" refers to a molecule that increases the intensity or prolongs the duration of the biological activity thereof. This definition includes, moreover, those compounds or molecules which allow for the expression of a nucleotide sequence that encodes for a GSE 24.2 protein. An activator compound may be composed of a peptide, a protein or a nucleotide sequence.

Thus, a particular embodiment of the invention is a nucleotide sequence, hereinafter GSE 24.2 gene sequence of this invention, which allows for the expression of a protein or peptide that induces the recovery of telomerase activity in the interior of the cells of a mammal, preferably human, and which is composed of one or several sequences of GSE 24.2 nucleotides belonging to the following group:
   a) a nucleotide sequence composed of a human GSE 24.2 nucleotide sequence (SEQ ID NO1),
   b) a nucleotide sequence analogous to the sequence of a),
   c) a fragment of any of the sequences of a) and b), and
   d) a nucleotide sequence, genetic construct, that comprises any sequence belonging to a), b) and c).

In the sense used in this description, the term "analogous" is intended to include any nucleotide sequence that may be isolated or constructed on the basis of the sequence shown in this specification; for example, by introducing conservative or non-conservative nucleotide substitutions, including the insertion of one or more nucleotides, the addition of one or more nucleotides at any of the ends of the molecule or the deletion of one or more nucleotides at any end or in the interior of the sequence, which allows for the encoding of a peptide or protein capable of mimicking the activity of the GSE 24.2 sequence (SEQ ID NO2) or fragments thereof (SEQ ID NO12 and SEQ ID NO14).

The dyskerin enzyme belongs to a family of pseudouridine synthase present in several organisms (see FIG. 3B, Mitchel et al., 1999). On the basis of the information described in this invention and of different organisms found in nature, a person skilled in the art may isolate or construct a nucleotide sequence analogous to those described in this invention.

In general, an analogous nucleotide sequence is substantially homologous to the nucleotide sequence described above. In the sense used in this description, the expression "substantially homologous" means that the nucleotide sequences in question have a degree of identity of, at least, 30%, preferably of, at least, 85%, or more preferably of, at least, 95%.

As used in this invention, the term "nucleotide sequence" refers to a DNA, cDNA or mRNA sequence.

A particular embodiment of this invention is the nucleotide sequence of the GSE 24.2 sequence of a) composed of SEQ ID NO1.

Another particular embodiment of this invention is the nucleotide sequence of the GSE 24.2 sequence of b) composed of SEQ ID NO11 or SEQ ID NO13, which encode the Trub I and Trub II peptide domains, respectively (Example 1.7).

The GSE 24.2 nucleotide sequence identified as d) corresponds to a GSE 24.2 gene construct. This GSE 24.2 gene construct of the invention may also comprise, if necessary and in order to allow for better isolation, detection or cytoplasm secretion of the expressed peptide, a nucleotide sequence that encodes a peptide susceptible to being used for purposes of isolation, detection or secretion of said peptide. Therefore, another particular embodiment of this invention is a GSE 24.2 genetic construct that comprises, in addition to the GSE 24.2 nucleotide sequence, any other nucleotide sequence that encodes a peptide or peptide sequence which allows for the isolation, the detection or the cell cytoplasm secretion of the expressed peptide; for example, for illustrative purposes and without this limiting the scope of the invention, a polyhistidine sequence (6×His), a peptide sequence that is recognisable by a monoclonal antibody (for example, for the identification thereof, or any other that may be used to purify the resulting fusion protein by immunoaffinity chromatography: tag peptides such as c-myc, HA, E-tag) ("Using antibodies: a laboratory manual". Ed. Harlow and David Lane (1999). Cold Spring Harbor Laboratory Press. New York. Chapter: Tagging proteins. Pp. 347-377).

The GSE 24.2 nucleotide sequence and the GSE 24.2 genetic construct described above may be obtained by a person skilled in the art using techniques that are widely known in the state of the art (Sambrook et al. "Molecular cloning, a Laboratory Manual". 2nd ed., Cold Spring Harbor Laboratory Press, N.Y., 1989. vols. 1-3). Said nucleotide sequences may be integrated in a gene expression vector that allows for the regulation of the expression thereof under suitable conditions in the interior of cells.

Therefore, another particular embodiment of this invention is a GSE 24.2 expression vector that comprises a GSE 24.2 nucleotide sequence or a GSE 24.2 genetic construct, described in this invention, which allows for the expression of a protein or peptide capable of recovering telomerase activity in the interior of cells of mammals, preferably humans. One example of a particular embodiment is the pLNCX 24.2 expression vector of the invention (see examples 1 and 2).

In general, an expression vector comprises, in addition to the GSE 24.2 nucleotide sequence or the 24.2 genetic construct described in the invention, a promoter that directs the transcription thereof (for example, pT7, plac, ptrc, ptac, pBAD, ret, etc.), whereto it is operatively bound, and other necessary or appropriate sequences which control and regulate said transcription and, if applicable, the translation of the product of interest; for example, transcription initiation and termination signals (tlt2, etc.), polyadenylation signal, replication origin, ribosome-binding sequences (RBS), transcriptional-regulator-encoding sequences (enhancers), transcriptional silencers, repressors, etc. Examples of appropriate expression vectors may be selected, on the basis of the conditions and needs of each specific case, amongst expression plasmids, viral vectors (DNA or RNA), cosmids, artificial chromosomes, etc., which may contain, in addition, markers that may be used to select the cells transfected or transformed with the gene or genes of interest. The selection of the vector will depend on the host cell and the type of use intended. Therefore, in accordance with a particular embodiment of this invention, said vector is a plasmid or a viral vector. Said vector may be obtained by conventional methods known by those skilled in the art; similarly, different widely-known methods may be used for the transformation of microorganisms and eukaryotic cells—chemical transformation, electroporation, microinjection, etc., which are described in various manuals [Sambrook, J., Fritsch, E. F., and Maniatis, T. (1989). Molecular cloning: a laboratory manual. 2nd ed. Cold Spring Harbor Laboratory, Cold Spring Harbor, N.Y.].

In addition, another particular embodiment of the invention is a protein or peptide, hereinafter GSE 24.2 protein of this invention, that exhibits activity aimed at recovering telomerase actions in the interior of the cells of a mammal, preferably human, and which comprises one or several amino acid sequences belonging to the following group:
   a) an amino acid sequence composed of a human GSE 24.2 amino acid sequence (SEQ ID NO2),
   b) an amino acid sequence analogous to the sequence of a),
   c) a fragment of any of the sequences of a) and b), and
   d) an amino acid sequence that comprises any sequence belonging to a), b) and c).

In the sense used in this description, the term "analogous" is intended to include any amino acid sequence that may be isolated or constructed on the basis of the sequence shown in this specification; for example, by the introduction of conservative or non-conservative amino acid substitutions, including the insertion of one or more amino acids, the addition of one or more amino acids at any of the ends of the molecule or the deletion of one or more amino acids at any end or in the interior of the sequence, and which mimics the telomerase recovery activity of SEQ ID NO2.

The dyskerin enzyme belongs to a family of pseudouridine synthase present in several organisms (see FIG. 3B, Mitchel et al., 1999). On the basis of the information described in this invention and of different organisms present in nature, a person skilled in the art may isolate or construct an amino acid sequence analogous to those described in this invention.

In general, an analogous amino acid sequence is substantially homologous to the amino acid sequence discussed above. In the sense used in this description, the expression "substantially homologous" means that the amino acid sequences in question have a degree of identity of, at least, 30%, preferably of, at least, 85%, or more preferably of, at least, 95%.

Another particular embodiment of this invention is a protein whose amino acid sequence of a) is composed of SEQ ID NO2.

Another particular embodiment of this invention is a protein whose amino acid sequence of c), fragment of which is composed of SEQ ID NO12 or SEQ ID NO14.

On the other hand, an additional embodiment of this invention comprises genetically modified cells, either eukaryotic—preferably human—or prokaryotic, hereinafter GSE 24.2 cells of the invention, which comprise the GSE 24.2 nucleotide sequence, construct, and expression vector of the invention and wherein the GSE 24.2 peptide or protein of the invention may be adequately expressed. These cells may be transformed, infected or transfected by means of said nucleotide sequences using genetic engineering techniques known by those skilled in the art [Sambrook, J., Fritsch, E. F., and Maniatis, T. (1989). Molecular cloning: a laboratory manual, 2nd ed. Cold Spring Harbor Laboratory] and are a part of this invention. These cells may be useful for the production of peptides capable of recovering telomerase activity, which may form the basis for a pharmaceutical composition, for the recombinant amplification of said nucleotide sequences, or may be useful per se as cells for gene therapy, etc. A particular embodiment would be a human cell transformed by these GSE 24.2 nucleotide sequences, from different cell strains, which may be used as cells for human tissue regeneration.

Gene expression systems may or may not allow for the integration of new genetic material into the host cell's genome. Thus, the GSE 24.2 nucleotide sequence, gene construct or expression vector may be used as a drug to protect host cells, preferably human cells affected by an alteration of telomerase activity, in a gene therapy method of treatment and prophylaxis for a human being affected by a disease that develops with alterations of telomerase activity. Similarly, the GSE 24.2 cells of the invention may be used as a drug for the regeneration or implantation of tissues or cells in human beings. The biopharmaceutical tools and gene therapy procedures are sufficiently known by those skilled in the art such that, with the information described in this invention, they may be developed relatively easily. Moreover, the proteins or peptides and the cells themselves may become biodrugs.

Therefore, another embodiment of the invention is the use of the GSE 24.2 activator compound of this invention in the preparation of a drug or pharmaceutical composition for the treatment of a disease caused by an alteration of, preferably a reduction in, telomerase activity, belonging, for illustrative purposes and without this limiting the scope of the invention, to the following group: ageing or acceleration of ageing, neurodegenerative diseases, dyskeratosis congenita, Cri du chat (CdC, OMIM 123450), ataxia telangiectasia (AT, OMIM 208900), Nijmegen Breakage Syndrome (NBS, OMIM 251260), Bloom Syndrome (BS, OMIM 10900), Werner Syndrome (WS, OMIM 277900), Fanconi's anaemia (FA OMIM 227650), ulcerous colitis, vascular ageing, atherosclerosis and cancer.

Studies performed in recent years have highlighted the potential relationship between defects in the maintenance of telomerase activity and other syndromes with bone marrow failures. The main cause of death for patients with dyskeratosis congenita is a bone marrow failure caused by opportunistic infections or haemorrhages (in 70% of the cases). Other causes of death are pulmonary disease and cancer.

Cri du chat disease (CdC, OMIM 123450) is a congenital hereditary syndrome associated with deletions of the short arm of chromosome 5 and appears with a frequency of 1:20,000 and 1:50,000; the frequency in patients affected by profound mental retardation (IQ less than 20) reaches 1%.

Ataxia telangiectasia (AT, OMIM 208900) is an autosomal recessive syndrome caused by mutations in the ATM gene. The problems appear between the second and fifth years of life and consist of progressive neuronal degeneration (cerebral ataxia), ocular telangiectasia, immunodeficiency, hypogonadism, genomic instability, premature ageing, mild diabetes mellitus, small height and predisposition to cancer (lymphomas and leukemias).

Nijmegen Breakage Syndrome (NBS, OMIM 251260) is an autosomal recessive disease caused by mutations or losses of the Nibrin gene. The syndrome is characterised by microcephalia, destructive facial appearance, retarded growth, progressive mental retardation and strong predisposition to lymphomas and respiratory tract infections.

Bloom Syndrome (BS, OMIM 210900) and Werner Syndrome (WS, OMIM 277900). BS is an autosomal recessive syndrome induced by mutations in the recQ gene, a protein with helicase activity. WS is also an autosomal recessive syndrome caused by mutations in helicase recQL2. Both diseases are characterised by accelerated ageing and the symptoms include atherosclerosis, osteoporosis, diabetes mellitus, binocular cataracts and predisposition to some types of tumours, particularly sarcomas (WS) and leukemias (BS).

Fanconi's anaemia (FA, OMIM 227650) is an autosomal recessive disease characterised by a great number of developmental defects, bone marrow failures and a one-thousand-fold increase in the incidence of myeloid leukemias and a strong predisposition to develop solid tumours. The frequency of development of the disease amongst mutation carriers is 1:100.

Ulcerous colitis is a disease which affects one in 100 Spaniards. It is believed to have an autoimmune origin wherein genetic and environmental factors intervene. Ulcerous colitis affects the small intestine and is characterised by chronic inflammation of the colonic sheet, with consequent ulceration, disruption of the mucous barrier and atrophia of the colon mucous membrane. The risk of cancer increases with the duration of the disease and occurs in numerous organs, such as the colon and lymphomas.

On the other hand, the consequences of cellular senescence include atherosclerosis. On the one hand, telomeric dysfunction is present in blood vessels with atherosclerotic plaques. The reactivation of telomerase in vascular progenitor cells increases these cells' division capacity and vasculogenesis. A loss of these progenitor cells contributes to an important vascular dysfunction; therefore, an anti-senescence therapy would provide a new approach to palliate the vascular effects of ageing and atherosclerosis.

Finally, in relation to other potential applications of the GSE 24.4 element of the invention, it is noted that the applications may be very broad once the mechanism, or one of the mechanisms, is known whereby this element carries out its biological activity, which is described for the first time in this invention: binding to the NHEIII region. In this area, there are few examples of this polypurine sequence in other promoters, but the fact that this polypurine region is located in the promoter regions of the CCR5 and PDGFA genes, amongst others, is highlighted. On the other hand, few transcription factors that interact with this NHE domain are known, although the nm23H1 metastasis-suppressing peptide is highlighted (Yoshiro O et al., 2001; Grand et al., 2004). In this regard, the GSE 24.2 element of the invention could be used as a suppressing factor for tumour growth and metastasis propagation, an application that is a part of this invention.

As used in this invention, the term "neurodegenerative disease" refers to a disease belonging, amongst others, for illustrative purposes, to the following group: Alzheimer's disease, Parkinson's disease, cerebellar ataxia and spinal cord degeneration.

Another embodiment of this invention is a pharmaceutical composition or drug for the treatment of diseases, disorders or pathologies that develop with alterations of telomerase activity, preferably a reduction in activity, hereinafter the pharmaceutical composition of this invention, that comprises a therapeutically effective quantity of a compound or agent capable of recovering telomerase activity jointly with, optionally, one or more pharmaceutically acceptable adjuvants and/or vehicles, which is capable of stimulating the generation and maintenance of telomerase activity.

The pharmaceutically acceptable adjuvants and vehicles that may be used in said compositions are the adjuvants and vehicles known by those skilled in the art which are habitually used in the preparation of therapeutic compositions.

In the sense used in this description, the expression "therapeutically effective quantity" refers to the quantity of the agent or compound capable of recovering telomerase activity calculated to produce the desired effect and, in general, it will be analyzed, amongst other causes, by the compounds' characteristics, including the patient's age and condition, the severity of the alteration or disorder, and the route and frequency of administration.

In another particular embodiment, said therapeutic composition is prepared in solid form or aqueous suspension, in a pharmaceutically acceptable diluent. The therapeutic composition provided by this invention may be administered by any appropriate administration route; to this end, said composition will be formulated in the suitable pharmaceutical form for the selected administration route. In a particular embodiment, administration of the therapeutic composition provided by this invention is performed by parenteral route, by oral route, by intraperitoneal route, subcutaneous route, etc. A review of the different pharmaceutical forms for drug administration and the necessary excipients to obtain them may be found, for example, in "Tratado de Farmacia Galénica", C. Faulí i Trillo, 1993, Luzán 5, S. A. Ediciones, Madrid.

Another particular embodiment of this invention is a pharmaceutical composition of the invention wherein the compound or agent capable of recovering telomerase activity belongs to the following group: GSE 24.2 sequence, genetic construct or vector which allow for the expression of a protein or peptide capable of recovering telomerase activity in the interior of the cells of a mammal, preferably human.

A particular embodiment of the invention is a pharmaceutical composition of the invention wherein the compound or agent capable of recovering telomerase activity is one or several GSE 24.2 sequences belonging to the following group:
  a) a nucleotide sequence composed of a human GSE 24.2 nucleotide sequence (SEQ ID NO1),
  b) a nucleotide sequence analogous to the sequence of a),
  c) a fragment of any of the sequences of a) and b), and
  d) a nucleotide sequence, genetic construct, that comprises any sequence belonging to a), b) and c).

Another particular embodiment of this invention is the pharmaceutical composition of the invention wherein the nucleotide sequence of a) is the GSE 24.2 nucleotide sequence (SEQ ID NO1).

Another particular embodiment of this invention is the pharmaceutical composition of the invention wherein the nucleotide sequence of c) is the SEQ ID NO11 or SEQ ID NO 13 nucleotide sequence.

Another particular embodiment of this invention is a pharmaceutical composition of the invention wherein the nucleotide sequence is a vector, preferably the pLNCX 24.2 vector.

Another particular embodiment of this invention is a pharmaceutical composition of the invention wherein the compound or agent capable of recovering telomerase activity is a protein or a peptide encoded by the GSE 24.2 sequence, genetic construct or vector of the invention.

A particular embodiment of the invention is a pharmaceutical composition of the invention wherein the GSE 24.2 protein or peptide belongs to the following group:
  a) an amino acid sequence composed of a human GSE 24.2 amino acid sequence (SEQ ID NO2),
  b) an amino acid sequence analogous to the sequence of a),
  c) a fragment of any of the sequences of a) and b), and
  d) an amino acid sequence that comprises any sequence belonging to a), b) and c).

Another particular embodiment of this invention is the pharmaceutical composition of the invention wherein the amino acid sequence of a) is the SEQ ID No2 sequence.

Another particular embodiment of this invention is the pharmaceutical composition of the invention wherein the amino acid sequence of c) is the SEQ ID NO12 or SEQ ID NO14 sequence.

Another particular embodiment of this invention is a pharmaceutical composition of the invention wherein the compound or agent that activates telomerase is a cell, preferably human, that is transformed by the GSE 24.2 sequence, construct or vector.

Another embodiment of the invention is the use of the pharmaceutical composition of the invention, hereinafter use of the pharmaceutical composition of the invention, in a method of treatment or prophylaxis for a mammal, preferably a human being, affected by a disease, disorder or pathology that develops with alterations of telomerase activity, consisting of the administration of said therapeutic composition in a suitable dose that allows for the recovery of telomerase activity in the interior of its cells.

The pharmaceutical composition of this invention may be used in a treatment method in isolation or jointly with other pharmaceutical compounds.

Another particular embodiment of this invention is the use of the pharmaceutical composition of the invention in a treatment method for a disease or disorder that develops with alterations of telomerase activity and which affects human beings, belonging, for illustrative purposes and without limiting the scope of the invention, to the following group: ageing or acceleration of ageing, neurodegenerative diseases, dyskeratosis congenita, Cri du chat (CdC, OMIM 123450), ataxia telangiectasia (AT, OMIM 208900), Nijmegen Breakage Syndrome (NBS, OMIM 251260), Bloom Syndrome (BS, OMIM 210900), Werner Syndrome (WS, OMIM 277900), Fanconi's anaemia (FA OMIM 227650), ulcerous colitis, vascular ageing, atherosclerosis and cancer.

Another particular embodiment of this invention is the use of the pharmaceutical composition of the invention in a treatment method for a neurodegenerative disease belonging to the following group: Alzheimer's disease, Parkinson's disease, cerebellar ataxia and spinal cord degeneration.

Another particular embodiment of this invention is the use of the pharmaceutical composition of the invention in a treatment method for the X-chromosome-linked form of dyskeratosis congenita.

Another particular embodiment of this invention is the use of the pharmaceutical composition of the invention in a treatment method for autosomal dominant dyskeratosis congenita.

Bibliographical References

Bednarek A, Shilkaitis A, Green A, Lubet R., Kelloff G, Christov K and Aldaz M. 1999. Suppression of cell proliferation and telomerase activity in 4-(hydroxyphenyl)retinamide-treated mammary tumors. Carcinogenesis. 20(5): 879-

Bessler M, Wilson D B, Mason P J. 2004. Dyskeratosis congenita and telomerase. Curr Opin Pediatr. February; 16(1):23-8. Review.

Burger A M, Double J A and Newell D R. 1997. Inhibition of Telomerase Activity by Cisplatin in Human Testicular Cancer Cells. Eur J. Cancer. 33(4): 638-44.

Cesare A J and Griffith J D. 2004. Telomeric DNA in ALT cells is characterized by free telomeric circles and heterogeneous t-loops. Mol. Cell. Biol. 24(22): 9948-9957.

Cheng H, Wu Z, Zheng J, Lu G, Yan J, Liu M, Huang D, Lin J. 2003. Inhibition on telomerase activity and cytotoxic effects by cisplatin in cultured human choroidal melanoma cells. Yan Ke Xue Bao. 19(1): 54-9.

Fu D, Collins K. 2003 Distinct biogenesis pathways for human telomerase RNA and H/ACA small nucleolar RNAs. Mol. Cell. 11 (5): 1361-72. Grand C L, Powell T J, Naglee R B, Bearss B J, Tye D, Gleason-Guzman M, Hurley L H. Mutations in the G-quadruplex silencer element and their relationship to c-MYC overexpression, NM23 repression, and therapeutic rescue. Proc Natl Acad Sci USA. 2004, 101 (16): 6140-6145.

Heiss N S, Knight S W, Vulliamy T J, Klauck S M, Wiemann S, Mason P J, Poustka A, Dokal I. 1998. X-linked dyskeratosis congenita is caused by mutations in a highly conserved gene with putative nucleolar functions. Nat. Genet. 19(1): 32-8.

Ishibashi T, Lippard S J. 1998 Telomere loss in cells treated with cisplatin. Proc Natl Acad Sci USA. 14; 95(8): 4219-23.

Jun Hyun KIM, Joo Hee KIM, Gun Eui Lee, Sang Woong KIM and In Kwon CHUNG. 2003. Identification of a quinoxaline derivative that is a potent telomerase inhibitor leading to cellular senescence of human cancer cells. Biochem J. 15; 373(Pt 2): 523-9.

Lemarteleur T, Gomez D, Paterski R, Mandine E, Mailliet P, Riou J F. 2004. Stabilization of the c-myc gene promoter quadruplex by specific ligands' inhibitors of telomerase. Biochem Biophys Res Commun. 22; 323(3): 802-8. Marrone A, Mason P J. 2003. Dyskeratosis congenita. Cell Mol Life Sci 60(3): 507-17. Review.

Mese H, Ueyama Y, Suzuki A, Nakayama S, Sasaki A, Hamakawa H, Matsumura T. 2001. Inhibition of telomerase activity as a measure of tumor cell killing by cisplatin in squamous cell carcinoma cell line. Chemotherapy. 47(2): 136-42.

Mitchell J R, Wood E, Collins K. 1999. A telomerase component is defective in the human disease dyskeratosis congenita. Nature. December 2; 402(6761): 551-5.

Mochizuki Y, He J, Kulkarni S, Bessler M, Mason P J. 2004. Mouse dyskerin mutations affect accumulation of telomerase RNA and small nucleolar RNA, telomerase activity, and ribosomal RNA processing. Proc Natl Acad Sci U S A. 20; 101 (29): 10756-61.

Oh S, Song Y H, Kim U J, Yim J, Kim T K. 1999. In vivo and in vitro analyses of Myc for differential promoter activities of the human telomerase (hTERT) gene in normal and tumor cells. Biochem Biophys Res Commun. 263(2):361-5.

Pan H, Agarwalla S, Moustakas D T, Finer-Moore J, Stroud R M. 2003. Structure of tRNA pseudouridine synthase TruB and its RNA complex: RNA recognition through a combination of rigid docking and induced fit. Proc Natl Acad Sci USA 28; 100(22):12648-53.

Poole J C, Andrews L G, Tollefsbol T O. 2001. Activity, function, and gene regulation of the catalytic subunit of telomerase (hTERT). Gene. 16; 269(1-2): 1-12. Review.

Redon S, Bombard S, Elizondo-Riojas M A, Chottard J C. 2001. Platination of the $(T2G4)_4$ telomeric sequence: a structural and cross-linking study. Biochemistry. 24; 40(29): 8463-70.

Roninson I B, Gudkov A V, Holzmayer T A, Kirschling D J, Kazarov A R, Zelnick C R, Mazo I A, Axenovich S, Thimmapaya R. 1995. Genetic suppressor elements: new tools for molecular oncology. Cancer Res. 15; 55(18): 4023-8.

Sanchez-Perez I, Murguia J R, Perona R. 1998. Cisplatin induces a persistent activation of JNK that is related to cell death. Oncogene 29; 16(4): 533-40.

Siddiqui-Jain A, Grand C L, Bearss D J, Hurley L H. 2002. Direct evidence for a G-quadruplex in a promoter region and its targeting with a small molecule to repress c-MYC transcription. Proc Natl Acad Sci USA. 3; 99(18):11593-8.

Sirinavin C and Trowbridge A. 1975. Dyskeratosis congenita: clinical features and genetic aspects. J. Med. Genet. 12, 339-354.

Sun D, Thompson B, Cathers B E, Salazar M, Kerwin S M, Trent J O, Jenkins T C, Neidle S, Hurley L H. 1997. Inhibition of human telomerase by a G-quadruplex-interactive compound. J Med. Chem. 4; 40(14):2113-6.

Trowbridge A A, Sirinavin C and Linman J W. 1977. Dyskeratosis congenita: hematologic evaluation of a sibship and review of the literature. Am. J. Hematol. 3, 143-152.

Wright W E, Shay J W, Piatyszek M A. 1995. Modifications of a telomeric repeat amplification protocol (TRAP) result in increased reliability, linearity and sensitivity. Nucleic Acids Res 25; 23(18): 3794-5.

Yoshiro O., Tanaka M, Yoshii S, Nakaya N K, Sugimora H. Tumor metastasis suppressor nm23H1 regulates Rac1 G interaction with Tiam1. Proc Natl Acad Sci USA 2001, 98 (8): 4385-4390.

Zhang R G, Zhang R P, Wang X W, Xie H. 2002. Effects of cisplatin on telomerase activity and telomere length in BEL-7404 human hepatoma cells. Cell Res 12(1): 55-62.

Zucchini C, Strippoli P, Biolchi A, Solmi R, Lenzi L, D'Addabbo P, Carinci P, Valvassori L. 2003. The human TruB family of pseudouridine synthase genes, including the Dyskeratosis Congenita 1 gene and the novel member TRUB1. Int J Mol. Med. 11 (6): 697-704.

EMBODIMENT EXAMPLES

Example 1

Identification and Biological Activity of the GSE 24.2 Sequence 1.1.—Identification of the GSE Sequence Called 24.2

Resistance to chemotherapy is one of the greatest limitations in the treatment of cancer. In order to analyze the mechanisms of resistance to cisplatin, cDNA library sequences that conferred resistance to cisplatin were isolated by tracking the gene suppression elements. This methodology, which has been previously described (Roninson et al., 1995), consists of the expression of cDNA constructs from a human placenta library, normalised in order to equate the abundance in gene expression. Close to 100 different clones that conferred resistance to cisplatin were isolated. After amplifying the cDNA inserts, they were subcloned in the pLNCX plasmid and transfected again in order to ensure that they conferred resistance. One of these GSEs was a 165-pb fragment called 24.2 (see SEQ ID NO1) which corresponded to an internal sequence of human dyskerin.

Figure 1:
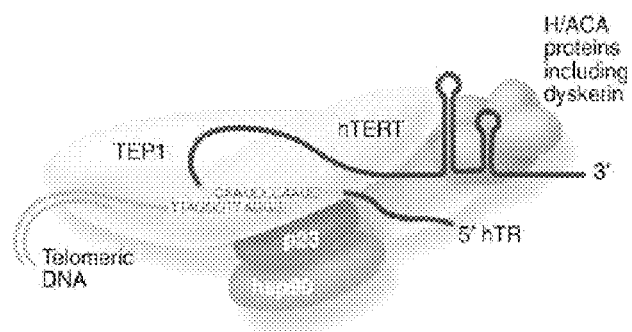
FIG. 1.—Schematic structure of the telomerase complex. The hTERT, dyskerin, p23, hsp90 and TEP1 proteins, jointly with the hTR RNA, constitute the ribonucleoprotein complex of telomerase.
Figure 2:
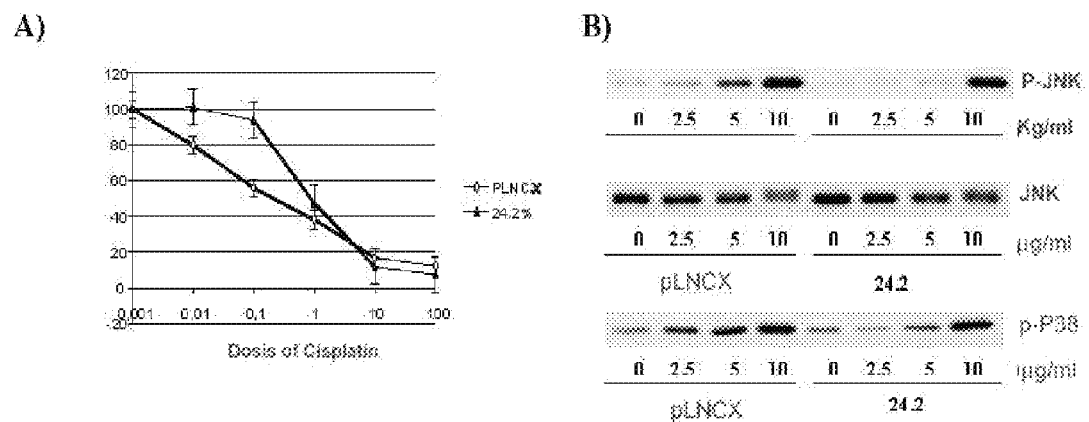
FIG. 2.—Cell viability and activation of the JNK and p38 death pathways in 293T cell lines: pLNCX and 24.2, treated with cisplatin. A) Cell viability. After seeding the 293T cells: expressing the empty vector (pLNCX) and GSE 24.2 (24.2) in 24-well plates, they were incubated with concentrations between 0-100 μg/ml of cisplatin. The cell viability was measured by means of the crystal violet technique after 72 hours of exposure to the drug. The data represent the mean of two experiments performed in quadruplicate. B) Activation kinetics. Treatment of both cell lines at the cisplatin concentrations indicated in the figure for 6 hours. Subsequently, the activation of JNK and p38 was studied using antibodies that specifically recognise the active forms. As a load control, the levels of JNK-1 were detected.

1.2.—Viability of the 293T Cell Lines: pLNCX and 24.2 with Respect to Cisplatin and Activation of the JNK and p38 Mediating Cell Death Pathways The pLNCX24-2 plasmid containing GSE of the same name was transfected in a stable manner in the 293T cells and, as a control, the pLNCX empty vector was transfected. After verifying, by means of PCR, that the 24.2 cell line contained this insert (data not shown), the response to cisplatin was studied, creating a viability curve with this drug. FIG. 2a shows the viability curve for the two cell lines in response to different doses of cisplatin after 72 hours. There the inventors observe that the cells that express GSE 24.2 in a stable manner exhibit greater viability in response to cisplatin as compared to those that express the empty vector, specially at low doses, close to the GSE selection dose. JNK and p38 are MAPKs that are activated in response to genotoxic agents (Sánchez-Perez et al., 1998). The activation kinetics of these two proteins in response to cisplatin is related to the capacity to induce cell death; for this reason, the activation of these kinases in the two cell lines was studied (FIG. 2b) and it was observed that a greater dose of cisplatin is required to activate both kinases in cells that express GSE 24.2 in a stable manner, thus suggesting that the expression of GSE 24.2 attenuates the cell damage signal that activates both kinases.

Figure 3:
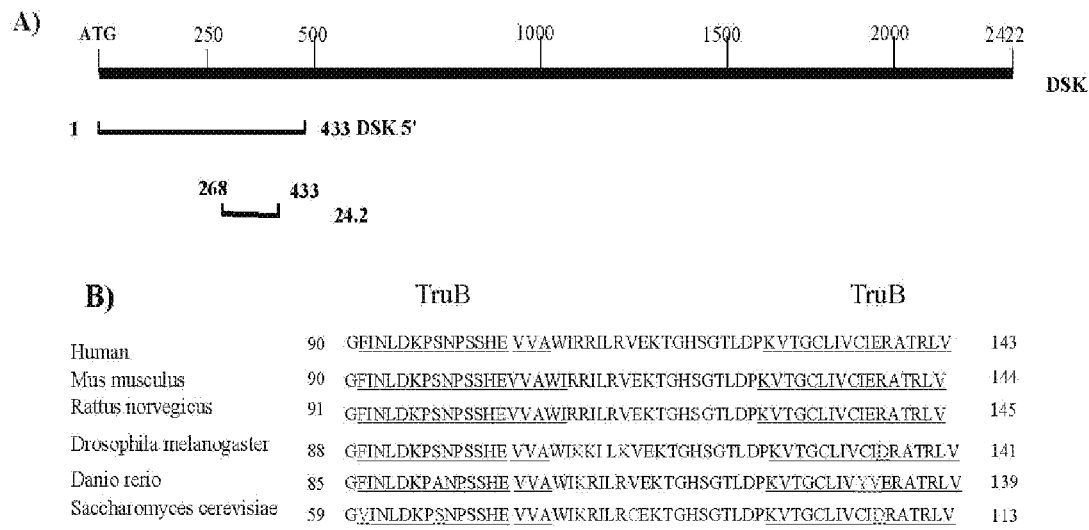
FIG. 3.—Diagram of the DSK sequences contained in the constructs used and sequence of genes homologous to DSK. A) Diagram of the cDNA of dyskerin. The GSE 24.2 element location is mapped from nucleotides 268 to 433, and the location of the DSK 5'construct is also shown. B) Comparative sequence in GSE 24.2 amino acids (SEQ ID NO: 15) with pseudouridine synthase amino sequences from other organisms including mus musculus (SEQ ID NO: 16), rattus norvegicus (SEQ ID NO: 17), drosophila melanogaster (SEQ ID NO: 18), danio rerio (SEQ ID NO: 19), and saccharomyces cerevisiae (SEQ ID NO: 20). The TRUB I and TRUB II conserved domains are shown.
Figure 4:
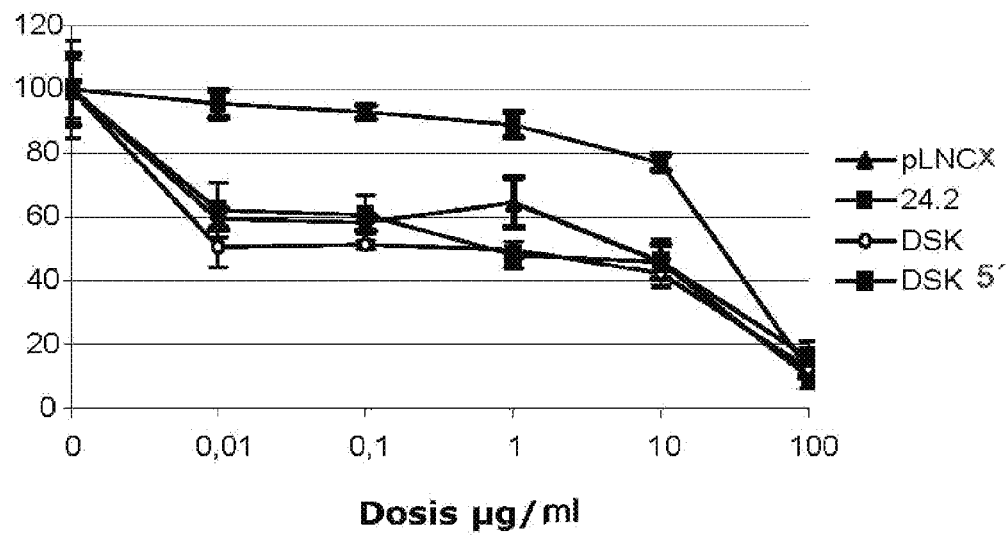
FIG. 4.—Viability of the 293T cell lines: pLNCX, 24.2, DSK5' and DSK treated with cisplatin. The cell lines described above (pLNCX and 24.2), the DSK 5' cell line, which expresses a fragment of dyskerin described in the preceding figure, and a fourth one that overexpresses the complete cDNA of dyskerin (DSK) have been used. The viability was analyzed as shown in FIG. 1 A. The data represent the mean of two experiments performed in quadruplicate.

1.3.—Viability of the 293T Cell Lines: pLNCX, DSK (Gene Bank NM 001363.2), DSK-5' and 24.2 in Response to Cisplatin In order to analyze whether the overexpression of dyskerin could reproduce the increase in cell viability in response to cisplatin induced by GSE 24.2, a cell line was generated which overexpressed, in a stable manner, the complete cDNA of dyskerin (pLNCX DSK). Also transfected was a construct that contained a fragment of dyskerin described in FIG. 3 a), which includes the GSE 24.2 sequence, in order to analyze whether the effect is exclusive of the region contained in 24.2 or a larger region of dyskerin (pLNCX DSK-5'). FIG. 4 shows the viability curve for the four cell lines in response to different doses of cisplatin. There the inventors observe that the cells that express the 24.2 construct (SEQ ID NO1) in a stable manner exhibit greater viability in response to cisplatin as compared to those that express the empty vector, complete dyskerin (DSK) or the 5' fragment of dyskerin (SEQ ID NO3). Therefore, it may be said that the increased viability in response to cisplatin is restricted to the cDNA sequence contained in the GSE 24.2 fragment.

1.4.—Telomerase Activity of the pLNCX and 24.2 Cell Lines Treated with Cisplatin As discussed above, cisplatin inhibits telomerase activity through a mechanism that is yet to be defined. Since GSE 24.2 corresponds to an internal sequence of dyskerin and the latter is a part of the ribonucleoprotein complex of telomerase, the effect of cisplatin on telomerase activity was analyzed in the cell line that expressed GSE 24.2; also analyzed was whether this effect varied with respect to the cell line that expresses the empty vector.

Figure 5:
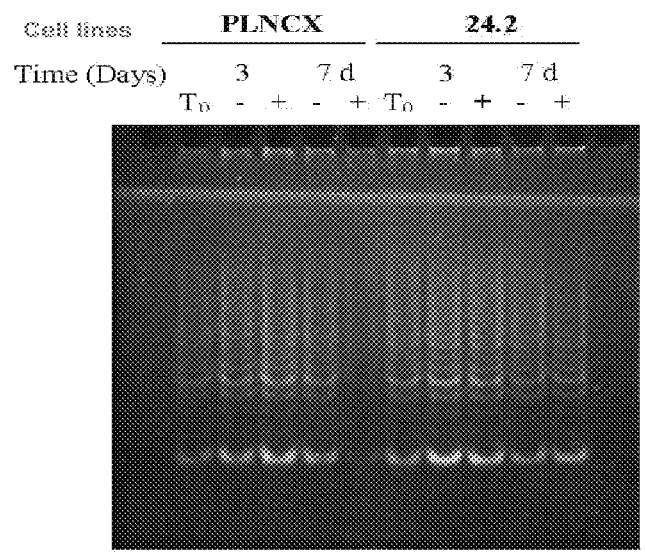
FIG. 5.—Telomerase activity of the 293T cell lines: pLNCX and 24.2 following treatment with cisplatin. The cells were seeded in 60-mm plates, pre-treated with 0.5 μg/ml of cisplatin for 3 days and subsequently treated with cisplatin at a dose of 3 μg/ml (unpretreated cells). The telomerase activity was measured by means of the Intergen TRAPeze assay. The experiment was performed 3 times, with similar results.

To this end, an assay of telomerase activity was performed using the TRAP method with the pLNCX and pLNCX 24.2 cell lines (FIG. 5), pre-treating them for 3 days with 0.5 µg/ml of cisplatin; subsequently, they were treated with 3 µg/ml of cisplatin for 3 and 7 days. The 3-day treatment was performed because it had been described that a specific inhibitor of telomerase needed to act during this time for efficient inhibition of the enzyme (Kim et al., 2003; Bednarek et al., 1999; Gowan et al., 2002). The 7-day treatment in the 293T pLNCX cells caused inhibition of telomerase activity, whereas no inhibition was observed for the 24.2 cell line during this time (FIG. 4). It can be concluded that the expression of GSE 24.2 confers resistance to the inhibition of telomerase activity caused by cisplatin and this inhibition is probably responsible for the greater survival capacity of these cells in response to the drug.

1.5.—Effect of the Inhibitor of Telomerase I in pLNCX and 24.2 Cells

Figure 6:
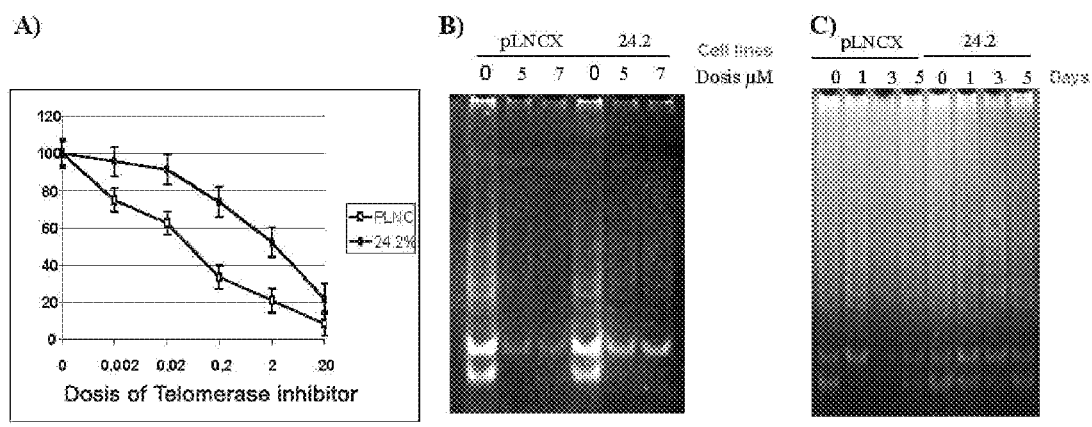
FIG. 6.—Cell viability and telomerase activity of the 293T cell lines: pLNCX and 24.2 treated with the Inhibitor of telomerase 1. A) Cell viability. After seeding the 293T cells: pLNCX and 24.2 in 24-well plates, they were incubated with concentrations between 0-20 μM of the Inhibitor of Telomerase I. The cell viability was measured by means of the crystal violet technique after 72 hours of exposure to the drug. The data represent the mean of two experiments performed in quadruplicate. B) Telomerase activity at different doses of the Inhibitor of Telomerase I. Telomerase activity of the 293T cells: 24.2 and pLNCX in the presence of different concentrations of the inhibitor of telomerase I (5-7 μM) for 3 days. The cells were seeded in 60-mm plates and subsequently treated at the specified concentrations and times. The telomerase activity was measured by means of the Intergen TRA-Peze assay. C) Telomerase activity at different times of treatment with the Inhibitor of Telomerase I. Telomerase activity in the presence of TII (5 μM) at 1 and 5 days. The cells were seeded as in B. Subsequently, they were treated with 5 μM of the Inhibitor at the specified times.

The Inhibitor of Telomerase I is a compound that forms G-quadruplexes in the telomeres, thereby inhibiting telomerase activity (Thompson et al., 1997). The effect of GSE 24.2 in response to the inhibitor of telomerase I was studied. To this end, a viability curve was performed wherein the pLNCX and 24.2 cell lines were treated with increasing concentrations of the inhibitor of telomerase I (0-20 µM) for 72 hours. FIG. 6a) shows that the 24.2 cells are more resistant to the inhibitor of telomerase I than parental cells. In order to verify whether this protection was accompanied by changes in the sensitivity of telomerase activity, said activity was studied in the pLNCX and pLNCX 24.2 cells treated with different doses of the Inhibitor of Telomerase I for 3 days (FIG. 6b). Inhibition of telomerase activity can be observed in the pLNCX cell line as being greater than in the pLNCX 24.2 cells. The telomerase activity was also studied by treating the pLNCX and pLNCX 24.2 cells with one dose (5 μM) and at several time points (0-5 days. FIG. 6c). In this case, it was also proven that the pLNCX 24.2 cells need greater exposure to the inhibitor in order for telomerase activity to be reduced. Therefore, the effects observed for telomerase activity and cell survival in both cell lines are common for cisplatin and the inhibitor of telomerase 1, thus suggesting that the GSE 24.2 fragment could have a significant role in the maintenance of the telomeres' structure, at least in part, since it is capable of preventing the inhibition caused by the inhibitor of telomerase 1.

Figure 7:
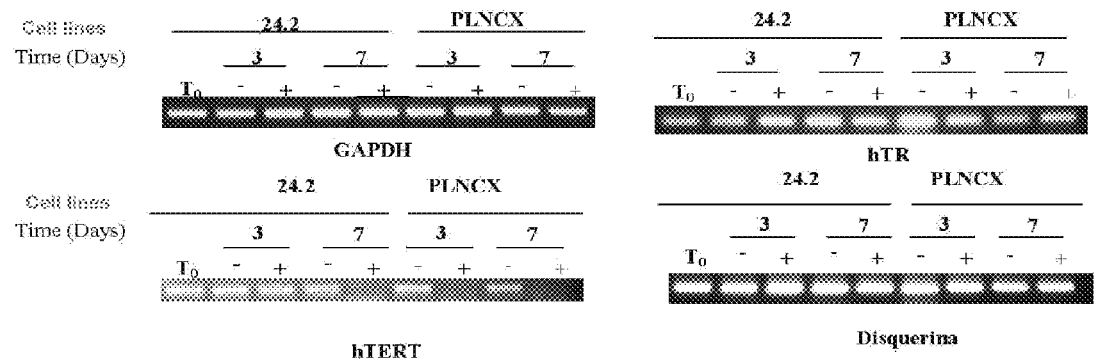
FIG. 7.—Expression levels of different genes related to telomerase in 293T cells: pLNCX and 24.2 following treatment with cisplatin. The cells were seeded in 60-mm plates, treated with 3 μg/ml of cDDP following pre-treatment with 0.5 μg/ml of cisplatin for 3 days and, subsequently, collected at the times specified in the figure (3 and 7 days). Following the extraction of RNA, RT-PCR was performed with oligos specific for hTERT, hTR and dyskerin in order to analyze the expression levels of the messenger RNAs. As a starting RNA control, oligos for the amplification of GAPDH were used.

1.6.—Effects of Cisplatin on the Expression Levels of hTR, hTERT and Dyskerin in the pLNCX and 24.2 Cell Lines One of the explanations for the lower sensitivity of pLNCX 24.2 cells to cisplatin could be a change in the levels of some of the components of the telomerase complex. Therefore, the expression levels of different genes involved in the telomerase complex and the effect that cisplatin had on their expression were studied. To this end, the pLNCX and pLNCX 24.2 cells were pre-treated with 0.5 μg/ml and treated with 3 μg/ml of cisplatin for 3 and 7 days. Using oligos specific for hTR, hTERT and dyskerin, the expression levels of these genes and the effect of cisplatin on said expression were studied. It was proven that cisplatin has no effect on the expression of dyskerin and hTR (FIG. 7); on the contrary, it was observed that, following 3 days of treatment, there is a reduction in the expression of hTERT in the pLNCX cells; on the other hand, there is no reduction in expression in the pLNCX 24.2 cells until 7 days of treatment. Therefore, the pLNCX 24.2 cells need greater exposure to cisplatin in order to exhibit inhibition of the expression of hTERT. This change in the sensitivity to cisplatin could explain, at least partially, the difference in sensitivity in the telomerase activity assays.

Figure 8:
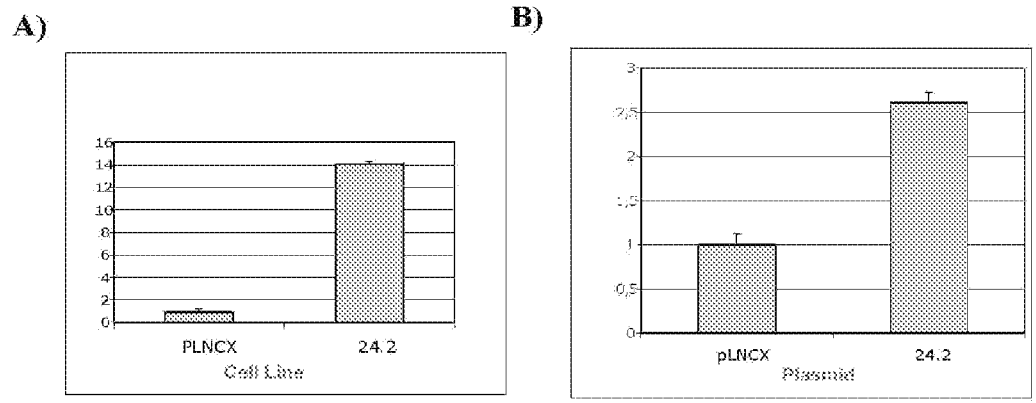
FIG. 8.—Activity of the hTERT promoter in the 293T cell lines: pLNCX and 24.2 and in 293T cells transiently transfected with the pLNCX-24.2 construct and the pLNCX empty plasmid. A) Both the pLNCX and the 24.2 cells were transiently transfected with 0.25 μg of the hTERT-luc reporter vector. The cells were seeded in 60-mm plates. After 24 hours of transfection, the cells were lysed and the luciferase activity of 10 μg of total protein was quantified. As a transfection control, the cells were co-transfected with a reporter vector, CMV-Renilla. B) The 293T cells were transfected with the pLNCX vector and the 24.2 plasmid (5 μg), and both were co-transfected with 0.25 μg of the hTERT-luc reporter vector. After seeding the cells as in A, they were transfected with pLNCX and 24.2, and co-transfected with the hTERT-luc reporter vector; subsequently, they were treated as in A. As a transfection control, the CMV-Renilla reporter vector was used. The data correspond to the ratio of relative units of luciferase with respect to non-transfected cells. Each point represents the mean the standard deviation obtained from 3 independent experiments. C) The 293T cells were transfected with the different GSE 24.4, DSK, TRUB I, TRUB II constructs and the pLNCX empty plasmid (5 μg), and co-transfected with 0.25 μg of the hTERT-luc reporter vector. The cells were seeded in 60-mm plates; after 24 hours of transfection, the cells were lysed and the luciferase activity of 10 μg of total protein was quantified. As a transfection control, the cells were co-transfected with a CMV-Renilla reporter vector. The data correspond to the ratio of relative units of luciferase with respect to non-transfected cells. Each point represents the mean±the standard deviation obtained from 3 independent experiments.

1.7.—Effect of the Expression of GSE 24.2 and Trub I and Trub II Fragments, in Both a Stable and a Transient Manner, on the Activity of the hTERT Promoter Since changes were observed in the expression levels of hTERT in those cells that expressed the GSE 24.2 peptide in response to cisplatin, the inventors decided to analyze whether the expression of the GSE 24.2 sequence and sequences of fragments thereof—containing the Trub I (SEQ ID NO11) and Trub II (SEQ ID NO 13) domains—had any effect on the activity of the hTERT promoter. The pseudouridine synthase TRUB domain of dyskerin comprises two structural subdomains: the Trub 1 and II motifs (Zucchini et al., 2003). These two domains are critical to maintain the global protein structure of dyskerin. Moreover, motif II contains at least one residue (asp125) that is essential for enzymatic activity. To this end, the hTERT-luc reporter vector containing a 3,402-pb sequence (Song et al., 1999) of the human hTERT promoter was transfected in the cell lines: pLNCX 24.2 and pLNCX. FIG. 8a) shows that, in the pLNCX 24.2 cell line, the activity of the hTERT promoter is greater than in the cells that express the empty vector (pLNCX). The same experiment was performed by transiently expressing GSE 24.2 in the 293T cells (FIG. 8b) and it was observed that the transient expression of GSE 24.2 also increases the activity of the hTERT promoter as compared to the cells transfected with the empty vector. On the other hand, this analysis was performed with the two fragments of GSE 24.2 that contain each of the Trub I (SEQ ID NO11) and Trub II (SEQ ID NO13) domains, respectively, in order to identify the smallest sequence with an activity similar to that of the GSE 24.2 fragment (FIG. 8c). The results show that the sequence contained in GSE 24.2, the sequences with TruB domains, act by activating the expression of the hTERT promoter.

In addition, the sequence of the CBF5 gene of yeast, *S. cerevisiae* CBF5, a sequence equivalent to that of GSE 24.2 (FIG. 3b), was subcloned in the pLNCX vector, and it was observed that the expression of said construct increased the activity of hTERT, but not that of the hTR promoter (data not shown), indicating a high degree of functional conservation in the activity of this domain of dyskerin.

1.8.—Effect of the Expression of GSE 24.2 on the hTERT Promoter in Cells Treated with Cisplatin.

Figure 9:
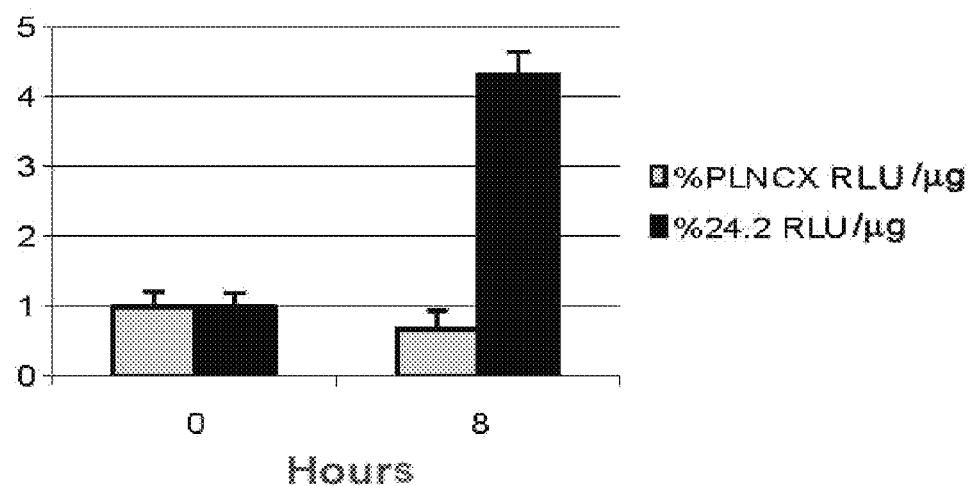
FIG. 9.—Activity of the hTERT promoter following treatment with cisplatin. A) Both the pLNCX cell line and the 24.2 cell line were transiently transfected with 0.25 μg of the hTERTluc reporter vector. After 24 hours of transfection, they were treated with 3 μg/ml of cisplatin for 8 hours. The cells were seeded in 60-mm plates; after 24 hours of transfection and following treatment with cDDP, the cells were lysed and the luciferase activity of 10 μg of total protein was quantified. As a transfection control, the cells were co-transfected with a CMV-Renilla reporter vector. B) 293T cells which, after being transiently transfected with pLNCX and 24.2, were co-transfected with 0.25 μg of the hTERT-luc reporter vector and treated as in A. After seeding the cells as in A, they were transfected with pLNCX and 24.2, and co-transfected with the hTERT-luc reporter vector; subsequently, they were treated as in A. As a transfection control, the CMV-Renilla reporter vector was used. The data correspond to the ratio of relative units of luciferase with respect to non-transfected cells. Each point represents the mean±the standard deviation obtained from 3 independent experiments.
Figure 9:
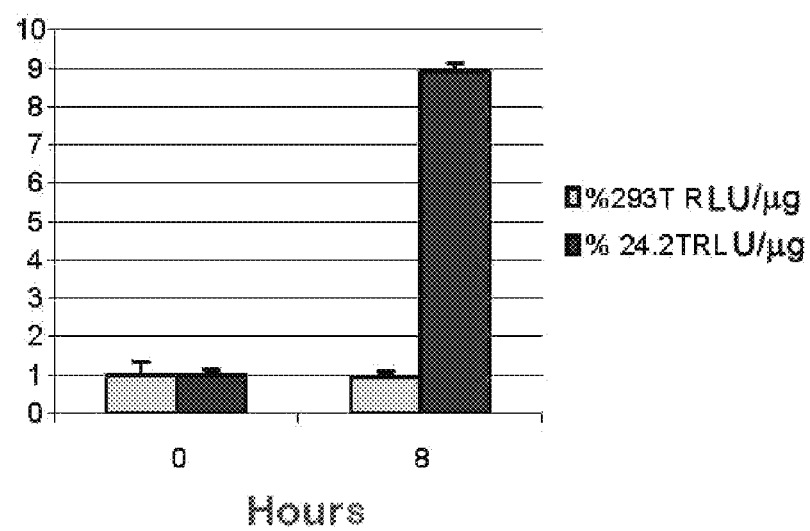

After observing that the expression of GSE 24.2 delayed the inhibition of the expression of hTERT induced by cisplatin, it was analyzed whether the treatment with cisplatin had any effect on the promoter of said gene and whether the expression of GSE 24.2 influenced the latter. To this end, the pLNCX and pLNCX 24.2 cells were transfected with the hTERT-luc reporter vector. After 24 hours of transfection, they were treated with 3 μg/ml of cisplatin for 8 hours and the telomerase activity was assayed (FIG. 9a). It can be observed that, in the pLNCX 24.2 cells, the induction of the activity of the promoter is 4 times greater than in the pLNCX cells following treatment with cisplatin. The same experiment was performed by transiently expressing GSE 24.2 and comparing them to the 293T cells transfected with the pLNCX empty vector. In this case, the activity of the cells that expressed GSE 24.2 was greater than the baseline activity following treatment with cisplatin.

Example 2

Figure 11:
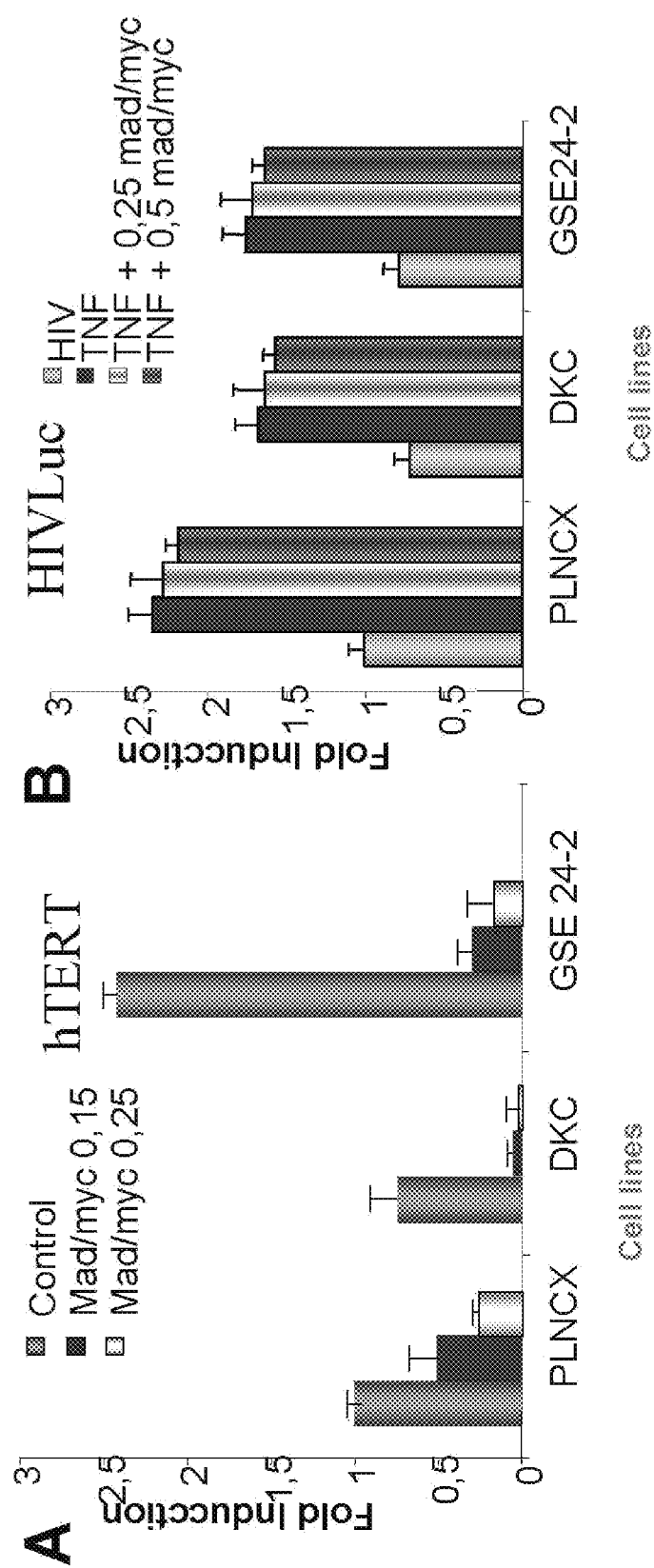
FIG. 11.—The GSE 24.2 peptide increases the activity of the hTERT promoter regulated by c-MYC. A) The 293T cells were co-transfected with different constructs (10 μg/DNA per million cells) and the hTERT-luc reporter (1 μg per million cells). B) The specified cell lines were co-transfected with the hTERT-luc reporter and different quantities of the Mad/myc expression vector. C) The specified cell lines were co-transfected with the HIV-luc reporter and with different quantities of the Mad/myc expression vector. After 24 h of transfection, the cells were stimulated with 50 ng/ml of TNF-α for 6 hours and the luciferase activity was analysed as described above. CMV-Renilla (0.1 μg/ml per million cells) was used as a control for the transfection efficiency. The data represent the mean of two experiments performed in quadruplicate.

The NHEIII Fragment of the Promoter of the c-MYC Gene is the Target of the GSE 24.2 Peptide The hTERT promoter contains two E-box regions (CACGTG), binding sites to myc/max heterodimers (Oh et al., 1999; Wu et al., 1999), as well as five sp1 regions. In order to analyze whether activation of the hTERT promoter by the GSE 24.2 peptide takes place through this E-box, a hybrid molecule containing this binding domain to c-myc DNA and the mad transactivation domain was transfected, which was capable of inhibiting binding to this E-box, thereby inhibiting the dependent transcription of c-myc. The control cells and cells that express the dyskerin protein (DKC) and the GSE 24.2 peptide were transfected with incremental quantities of said hybrid molecule. The expression of the mad/myc fusion protein inhibited the baseline activity of the hTERT promoter in a dose-dependent manner, in both the control group and the DKC cells. Furthermore, the expression of the myc/mad fusion protein was capable of blocking the GSE-24.2-peptide-mediated transcription in the GSE 24.2 cells, thus suggesting that the activation of the hTERT transcription induced by GSE 24.2 is dependent on c-myc (FIG. 11b). This inhibition was specific, since the transfection of the myc/mad construct jointly with an NFκB-dependent promoter (HIVLuc) did not affect the transcription following stimulation with TNFα in any of the cell lines (FIG. 11c).

Figure 12:
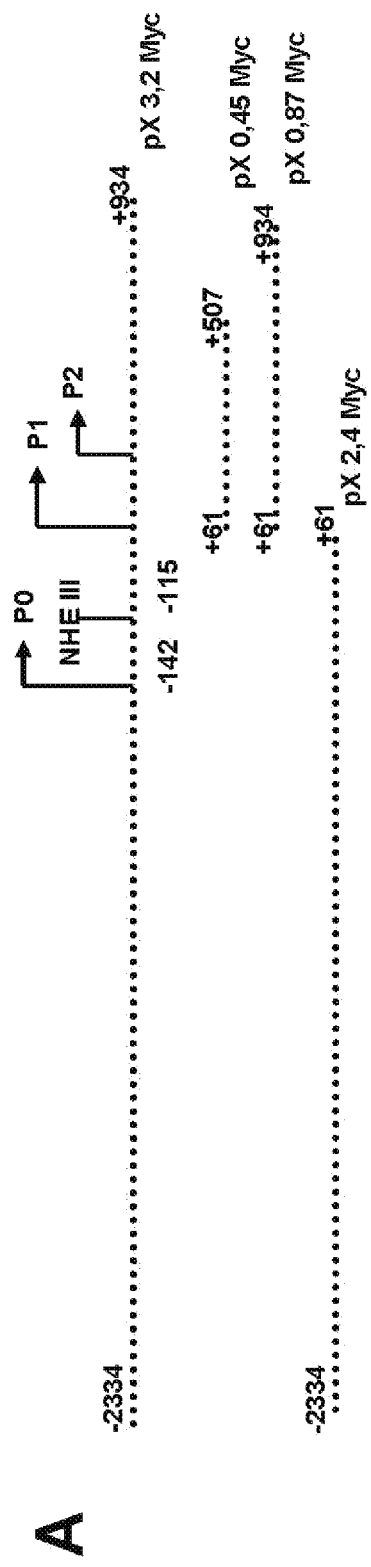
FIG. 12.—The promoter activity of c-MYC is induced by the GSE 24.2 peptide. A) Schematic representation of the c-MYC promoter, indicating the different constructs used in the experiments. B) 293T cells were co-transfected with the specified plasmids (10 μg/DNA per million cells) and with the px3.2 c-MYC-luc reporter (1 μg per million cells). C) The specified cell lines were transfected with the px3.2 c-MYC-luc reporter (1 μg per million cells). D) The specified cell lines were transfected with the different constructs of the c-MYC-luc reporter (1 µg per million cells). After 24 hours of transfection, the luciferase activity was analysed as specified above. CMV-Renilla (0.1 µg/ml per million cells) was used as a control for the transfection efficiency. The data represent the mean of two experiments performed in quadruplicate.
Figure 12:
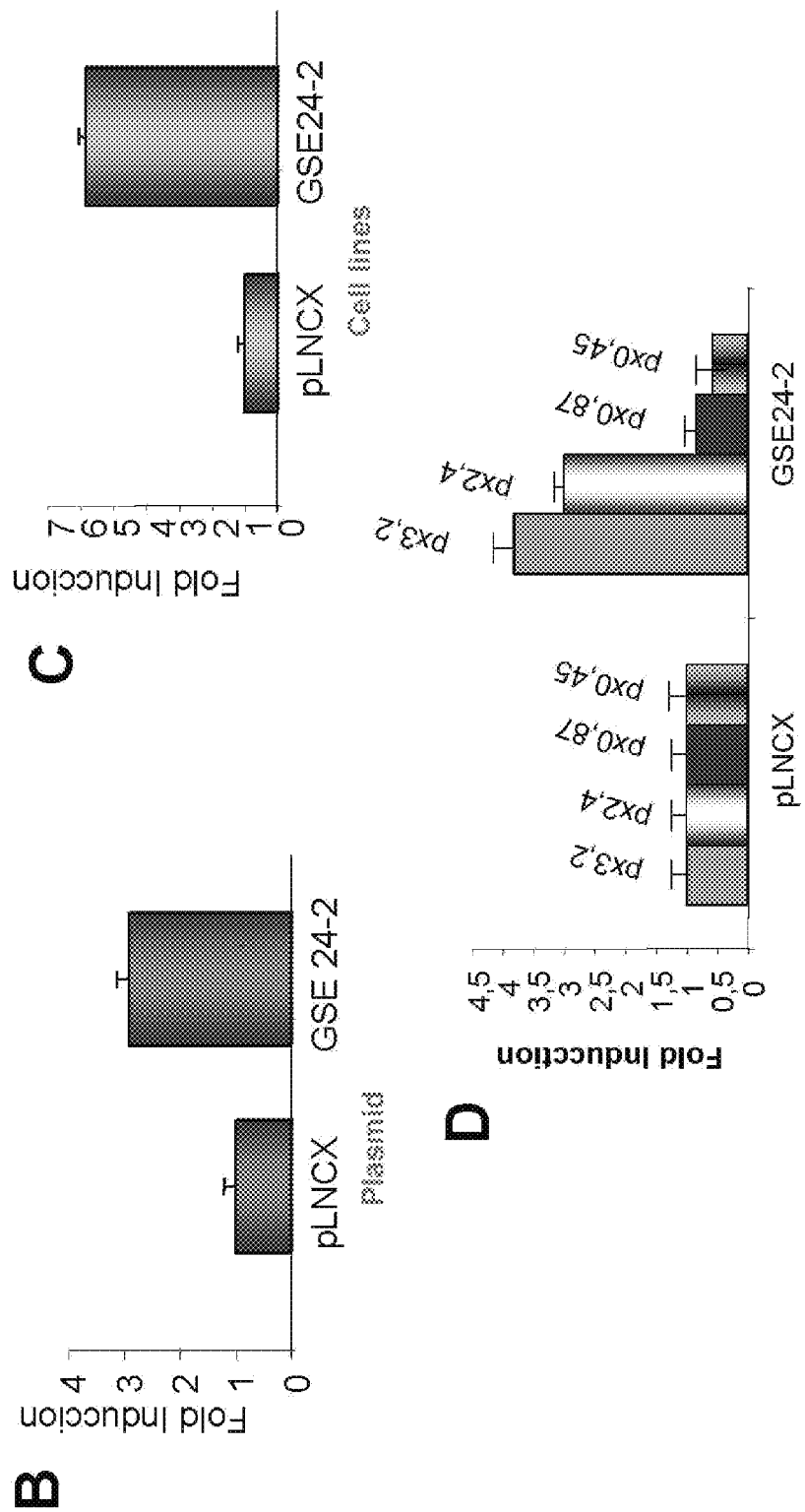

The transcription of the c-myc gene is controlled by two different promoters and it seems to be repressed by a domain hypersensitive to DNase located between the P0 and P1 promoters (NHEIII). Thus, four different constructs were used that contained 3.2 kb of the transcription initiation point of c-myc bound to the luciferase gene (FIG. 12a). This plasmid (px3.2myc) was transfected in the control cells and in the GSE 24.2 cells, and a three-fold increase in activity was observed in the last group of cells (FIG. 12b). A similar result was obtained when cells were transfected in 293T cells with the pLNCX vector or with the plasmid that expresses the GSE 24.2 peptide jointly with the px3.2myc reporter (FIG. 12c).

Both results indicated that this internal fragment of dyskerin (GSE 24.2) was capable of activating the transcription of the c-myc gene. This transcription factor, c-myc, should therefore activate the transcription of hTERT. Thus, three mutants deleted in the c-myc promoter were used to define the necessary region for the GSE 24.2 peptide to perform its inducing activity. Of all the mutants used, only those contained in the distal region of promoters P1 and P0, which include the NHEIII domain, were capable of maintaining the transcription in the GSE 24.2 cells, but not in the control cells (FIG. 12d), thus indicating that the proximal region of promoter P2 is not necessary for the activity of the GSE 24.2 peptide.

Figure 13:
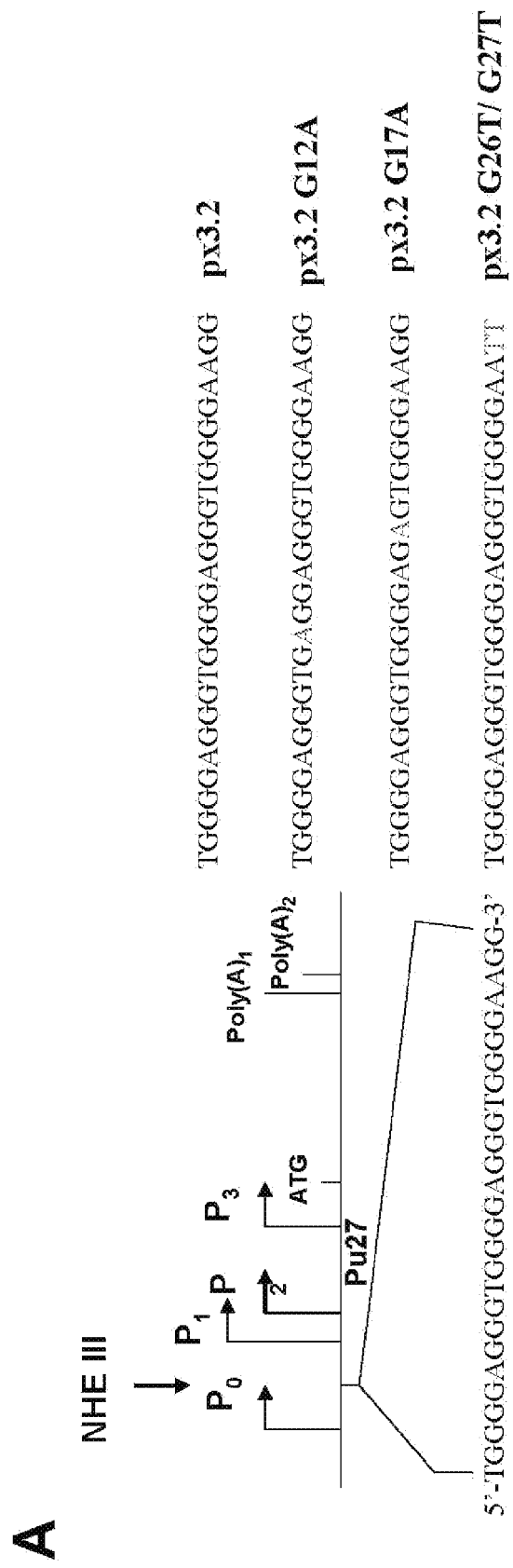
FIG. 13.—The activity of the c-MYC promoter induced by the GSE 24.2 peptide is dependent on the NHE III element. A) Schematic representation of the mutations generated in the NHE III element, px3.2 (SEQ ID NO: 21): px3.2 G12A (SEQ ID NO: 22), px3.2 G17A (SEQ ID NO: 23), and px3.2 G26T/G27T (SEQ ID NO: 24). B) The 293T cells were co-transfected with different constructs (10 µg/DNA per million cells) and with different mutants of the px3.2 reporter plasmid (1 µg per million cells). C) The cell lines specified in the figure were transfected with the different mutants of the px3.2 reporter (1 µg per million cells). After 24 h of transfection, the luciferase activity was analysed as specified above. CMV-Renilla (0.1 µg/ml per million cells) was used as a control for the transfection efficiency. The data represent the mean of two experiments performed in quadruplicate.
Figure 13:
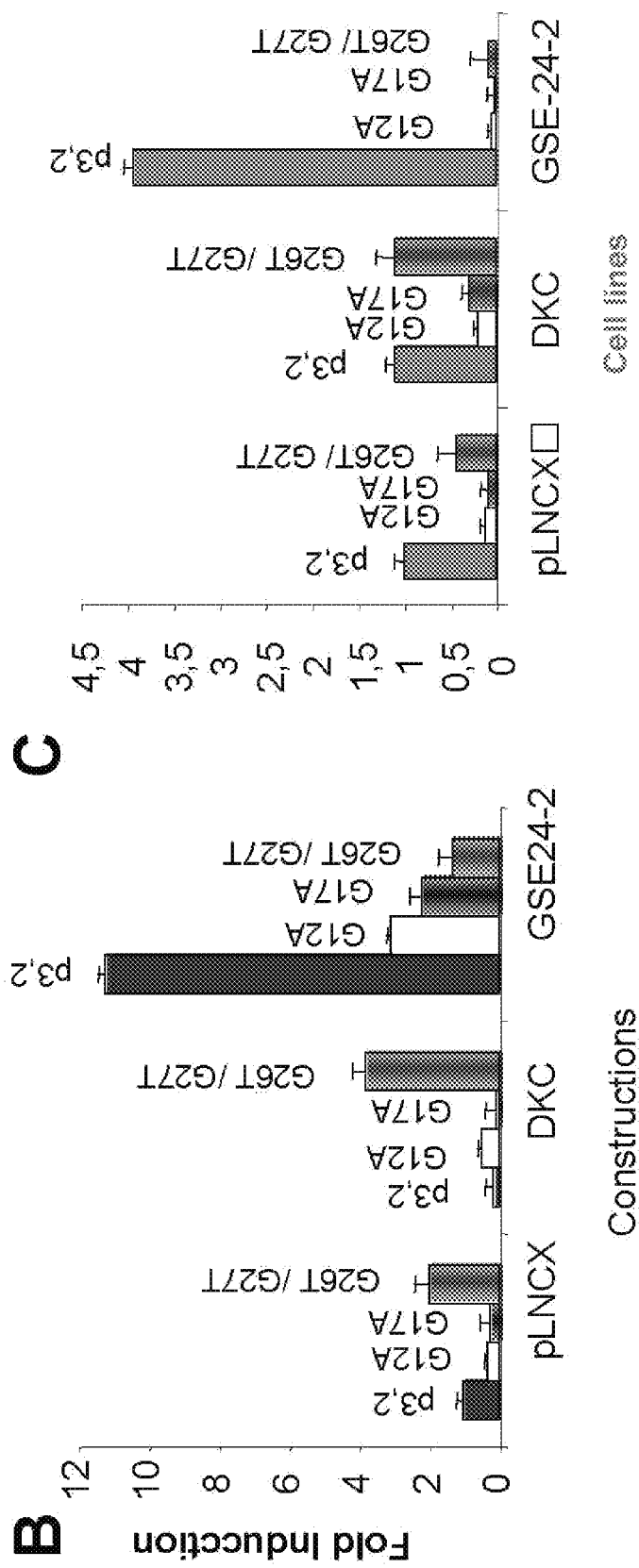

Since the NHEIII region has been described as an inhibitor of the transcription of c-myc, several mutants of the NHEIII region were constructed by Guanine modification of the purine-rich region. The 27 Guanines present in the NHEIII region are involved in maintaining the secondary structure of the G-quadruplexes of the purine-rich region (Pu27). The following were mutated: G12A, located on the second guanine of the second quartet; G17A, on the second triplet of Guanines; and, finally, two consecutive Guanines (G26A/G27A) at the end of the purine-rich region (FIG. 13a). These promoter constructs were transfected in cells that express, either the empty vector, or the vectors containing the DKC protein or the GSE 24.2 peptide. The results indicate that only the WT px3.2 myc promoter was capable of being activated when transfected with GSE 24.2. The three mutants in the Pu27 region were activated by means of GSE 24.2, albeit at very low levels (FIG. 13b).

Interestingly, the transfection of the double mutant of G in the control cells or those that express DKC was capable of showing increased activity in the promoter, indicating that this region is important to maintain a conformation that represses the promoter. Similar results were obtained in transient transfection assays in 293T cells when the different mutants were transfected with the empty vector, with the DKC protein or the GSE 24.2 peptide (FIG. 13c). Overall, these results suggest that the GSE 24.2 peptide is capable of modifying the secondary structure of the Pu27 region towards an active conformation, thus allowing for transcription of the c-myc gene.

Example 3

Figure 10:
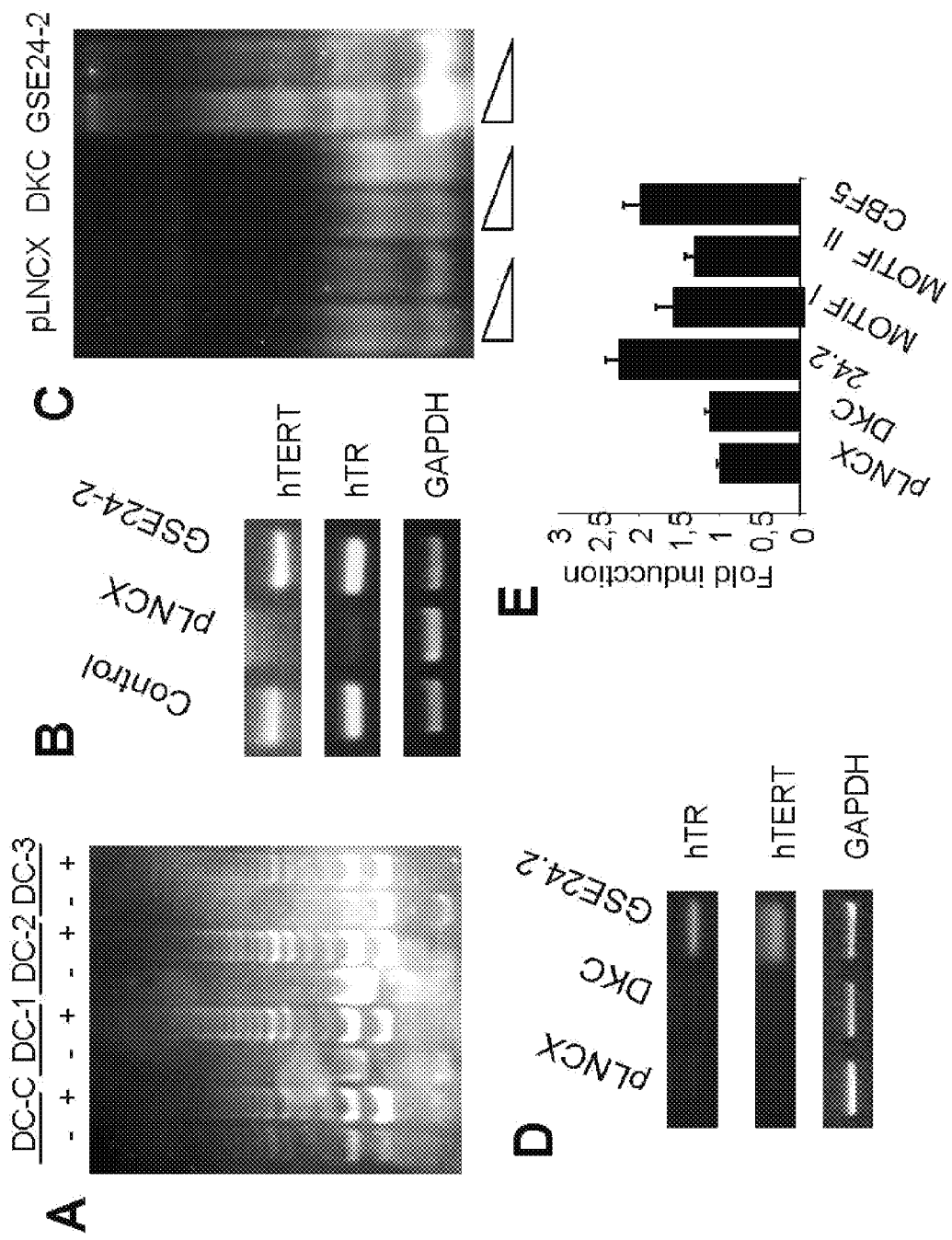
FIG. 10.—Telomerase activity and expression levels of hTERT and hTR in the cells of patients with dyskeratosis congenita and in VA13 cells transiently transfected with the 24.2 plasmid or the pLNCX empty vector. A) Telomerase activity measured by means of the TRAP assay in the cells of patients with dyskeratosis congenita (DC-1, DC-2 and DC-3) and in the carrier mother (DC-C) following electroporation of 45 μg of the pLNCX empty plasmid (−) or the pLNCX 24.2 vector (+) by 15 million cells. B) RT-PCR of the RNA from cells of one of the patients with dyskeratosis congenita, DC3 transfected with the empty vector and DC3 transfected with the 24.2 plasmid, using oligos specific for hTERT and hTR. As a starting RNA control, oligos for the amplification of GAPDH were used. C) Telomerase activity in VA13 cells. The cells were transiently transfected with 16 μg of the control pLNCX empty vector, expressing DKC or the GSE 24.2 peptide per million cells. 24 hours later, the telomerase activity was analysed as described above, using dilutions of the protein extracts from each transfection. D) The expression levels of hTERT and hTR in VA13 cells transfected with 16 μg of the different constructs per million cells. RNA levels were detected as described above. GAPDH was used as a control. In A, B, C, and D, the experiments were repeated three times with similar results. E) Activity of the hTERT promoter in VA13 cells. The cells were co-transfected with the specified constructs (10 μg per million cells) and with the hTERT-luc reporter (1 μg per million cells). After 24 h of transfection, the luciferase activity was analyzed as described above. CMV-Renilla (0.1 μg/ml per million cells) was used as a control for the transfection efficiency. The data represent the mean of two experiments performed in quadruplicate.

Expression of GSE 24.2 in the Cells of Patients with the X-Chromosome-Linked Form of Dyskeratosis Congenita and in VA13 Cells Since in the X-chromosome-linked form of dyskeratosis congenita there are defects in telomerase activity, with low levels of telomerase RNA, the effect of the expression of this GSE 24.2 was tested in the cells of patients with dyskeratosis congenita. To this end, cells of patients with dyskeratosis congenita (DC-1, DC-2, DC-3) and commercially available carrier mother cells (DC-C) were transfected with the GSE 24.2 vector or with the empty vector. These cells are mortal and normally age in cultivation. 24 hours after the transfection, the telomerase activity was measured and an increase in telomerase activity was observed in both the carrier mother cells and the cells of patients with dyskeratosis congenita when the GSE 24.2 fragment is expressed (FIG. 10a). Curiously, an increase in telomerase activity was not observed with the expression of complete dyskerin (data not shown). On the other hand, the levels of hTR are low in the DC cells that express a mutated form of the dyskerin gene (Mochizuki et al., 2004). It was investigated whether this increase in activity was the consequence of an increase in the expression of any of the components of the telomerase complex, hTERT and hTR. To this end, an RT-PCR assay was performed 24 hours after the transfection, using oligos specific for hTERT and hTR (FIG. 10b), and in both cases an increase in the expression levels was observed following expression of GSE 24.2.

Moreover, the expression of the GSE 24.2 peptide of the invention in the VA13 telomerase-deficient cell line (Cesare and Griffith, 2004) was capable of recovering telomerase activity (FIG. 10c), and the expression of the hTERT and hTR RNAs (FIG. 10d). In this cell line, the expression of motif I of the GSE 24.2 peptide (with a lower efficiency) and the fragment of the CBF5 gene of yeast additionally activated the hTERT promoter (FIG. 10e). Overall, the results indicate that the expression of the GSE 24.2 peptide was capable of recovering telomerase activity in both cell lines.

Materials and Methods

Constructs and cell lines. The cell lines of patients with X-chromosome-linked dyskeratosis congenita were obtained from the Corriel Cell Repository and kept in RPMI 20% FBS. The VA13 line was obtained from Dr. M Serrano. The DKC family was clinically described (Sirinavin et al., 1975; Trowbridge et al., 1977) and the affected individuals exhibit substitution of a T66A amino acid (data not shown) (DC-1, DC-2, DC-3). The carrier mother cell line (DC-C) expresses a messenger RNA without mutation (data not shown). These cells were grown in RPMI (Gibco) supplemented with 20% fetal bovine serum (Gibco) and 2 mM of Glutamine.

The DSK construct contains the complete cDNA of human dyskerin and the DSK 5' construct (SEQ ID NO5) contains the first 500 nucleotides of human dyskerin. Both constructs, like GSE 24.2 (SEQ ID NO1), were cloned in the ClaI site of the pLNCX plasmid (BD Biosciences Clontech).

The cells derived from patients with DC and their respective controls were transiently transfected by means of electroporation using 3 µg of the pLNCX or pLNCX 24.2 construct per million cells.

The 293T cell line was obtained from the American Type Culture Collection and the cells were grown in DMEM (Dulbecco's Modified Eagle's Medium) (Gibco) supplemented with 10% fetal bovine serum (Gibco) and 2 mM of Glutamine. This cell line was transfected in a stable manner using the calcium chloride method, 10 µg of plasmid per million cells. These cells were co-transfected with pBA-BEpur, 1 µg of vector per million cells. 24 hours after the transfection, the cells were treated with puromycin in order to select stable clones. It was confirmed that the cells expressed the GSE 24.2 fragment in a stable manner by means of PCR of the genomic DNA (data not shown).

The hTERT-luc construct was cloned in the pGL3 basic plasmid (Promega) and has been provided by Tae Kook Kim (Kim et al., 1999).

Drugs. Both cisplatin and the Inhibitor of Telomerase I were obtained from Calbiochem and used at the doses specified in each figure.

Telomerase activity assay based on the TRAP method (Wright et al., 1995). The telomerase activity was measured using the TRAPeze telomerase detection kit (Intergen) in accordance with the instruction manual. The protein concentration of each extract was quantified by means of the Bradford method using the BIORAD reagent and after performing a PCR in accordance with the manual instructions; polyacrylamide gel electrophoresis was performed with the reaction products under non-denaturing conditions and, subsequently, it was stained with Ethidium bromide for 30 minutes.

Total protein extraction. The cells were lysed after being washed with PBS in order to eliminate residue from the medium. The lysis buffer was prepared in accordance with standard protocols and the protein inhibitors were added: ABSF, orthovanadate, Leupeptin, pepstatin A, aprotinin and DTT (Sigma). Subsequently, the extracts were centrifuged at 14,000 rpm for 10 minutes at 4° C. and the supernatant was recovered. The total protein content was determined by means of the Bradford method using the BIORAD reagent.

Western Blot and antibodies. 20 µg of protein were separated in SDS-polyacrylamide gels; subsequently, they were transferred to Immobilon-P membranes (Millipore) by humid transfer. The membranes were blocked in a 5% BSA solution or in 5% skimmed milk in TBS (20 mM Tris-HCL, pH 7.5, 150 mM NaCl) 0.1% Tween-20 (Sigma). The membranes were incubated with the corresponding antibodies. The secondary antibodies used were anti-mouse/rabbit (Biorad), directly conjugated with peroxidase. The detection was performed by the ECL method (Pharmacia), as specified in the instruction manual.

The antibodies used for the assays were: anti-pJNK (V7391, Promega), anti-JNK1 (C-17, Santa Cruz Biotechnologies), anti p-P38 (C20, Santa Cruz Technologies).

Expression of genes by RT-PCR. Total RNA extraction from the cells was performed using the Trizol reagent (Life Technologies) following the manufacturer's instructions. In each reaction, 2 µg of total RNA were transcribed to cDNA using the M-Mlv reverse transcriptase (Promega).

The following oligos were used:

```
                                              (SEQ ID NO5)
Oligo A: 5'-CGGAAGAGTGTCTGGAGCAA-3'
and (SEQ ID NO6)
Oligo B: 5'-GGATGAAGCGGAGTCGGA-3';
for hTERT (SEQ ID NO7)
Oligo C: 5'-TCTAACCCTAACTGAGAAGGGCGTAG-3'
and (SEQ ID NO8)
Oligo D: 5'-GTTTGCTCTAGAATGAACGGTGGAAG-3';
for hTR
```

```
                                              (SEQ ID NO9)
Oligo E: 5'-ATGGCGGATGCGGAAGTAATT-3'
and (SEQ ID NO10)
Oligo F: 5'-CCCCTTCAATAGCATTGTGC-3'.
for dyskerin
```

The PCR conditions for the amplification of hTERT were the following: 94° C., 45 s; 60° C., 45 s; 72° C., 90 s for 31 cycles. The PCR conditions for hTR were: 94° C., 45 seconds; 55° C., 45 seconds; 72° C., 90 seconds for 28 cycles. The conditions for dyskerin were: 94° C., 40 seconds; 60° C., 60 seconds; 72° C., 120 seconds for 28 cycles (Zhang et al., 2002).

Luciferase assay. The transcriptional regulation of hTERT was measured by means of the Luciferase reporter gene, preceded by a 3,402-pb sequence of the hTERT promoter. After 24 hours of transfection, the cells were lysed with the commercial Reporter Lysis Buffer (Promega). The cell lysates were centrifuged and the expression of luciferase was quantified with 10 µg of protein from the supernatant, using a Berthold luminometer. A construct of the CMV promoter, followed by the renilla gene, was used as a transfection control. The luciferase activity is expressed per microgram of protein and is normalised using the luminescence of the renilla in the same extract.

Growth curves. The cell viability was studied by means of the crystal violet technique. The cells were seeded in 24-well plates and treated with different concentrations of the corresponding drug, specified in the figures. After 72 hours of incubation, the cells were fixated with 1% glutaraldehyde for 15 minutes and, after being washed with PBS, they were stained with 0.1% of the crystal violet colouring agent. The colouring agent associated with the cells was removed with a 10% acetic acid solution. The number of cells was determined by estimating the absorbance at 595 nm. The figures show the % viability with respect to the cells not subject to treatment and represent the mean of 2 experiments performed in quadruplicate with the corresponding deviations.

Directed mutagenesis. The specific mutations of guanine in the NHEIII region of the c-myc gene promoter, px3.2, were performed using the Quickchange X-L directed mutagenesis kit (Strategene) in accordance with the manufacturer's instructions.

The invention claimed is:

1. A protein or peptide that induces telomerase activity in the interior of the nucleus of a mammalian cell, wherein said protein or peptide is selected from the group consisting of:
   a. an amino acid sequence consisting of SEQ ID NO:2;
   b. an amino acid sequence consisting of SEQ ID NO:20;
   c. an amino acid sequence consisting of SEQ ID NO:12; and
   d. an amino acid sequence consisting of SEQ ID NO:14.

2. The protein or peptide of claim 1, wherein the protein or peptide is SEQ ID NO:2.

3. The protein or peptide of claim 1, wherein the protein or peptide is selected from the group consisting of SEQ ID NO:12 and SEQ ID NO:14.

4. A method of treating a disease caused by an alteration of telomerase activity, the method comprising the step of administering to a patient in need thereof a protein or peptide that induces telomerase activity in the interior of the nucleus of a mammalian cell, wherein said protein or peptide is selected from the group consisting of:
   a. an amino acid sequence consisting of SEQ ID NO:2;
   b. an amino acid sequence consisting of SEQ ID NO:20;
   c. an amino acid sequence consisting of SEQ ID NO:12; and
   d. an amino acid sequence consisting of SEQ ID NO:14.

5. The method of claim 4, wherein the disease is selected from aging, acceleration of aging, neurodegenerative diseases, and dyskeratosis congenita.

6. A method of treating a disease associated with a reduction in telomerase activity, the method comprising the step of administering to a patient in need thereof a protein or peptide that induces telomerase activity in the interior of the nucleus of a mammalian cell, wherein said protein or peptide is selected from the group consisting of:
   a. an amino acid sequence consisting of SEQ ID NO:2;
   b. an amino acid sequence consisting of SEQ ID NO:20;
   c. an amino acid sequence consisting of SEQ ID NO:12; and
   d. an amino acid sequence consisting of SEQ ID NO:14.

7. The method of claim 6, wherein the protein or peptide is SEQ ID NO:2.

8. The method of claim 1, wherein the protein or peptide is selected from the group consisting of SEQ ID NO:12 and SEQ ID NO:14.

* * * * *